United States Patent
Yoshiara et al.

(10) Patent No.: US 8,634,619 B2
(45) Date of Patent: Jan. 21, 2014

(54) MEDICAL IMAGE DIAGNOSIS APPARATUS AND IMAGE PROCESSING APPARATUS AND METHOD

(75) Inventors: Hiroki Yoshiara, Nasushiobara (JP); Naohisa Kamiyama, Otawara (JP); Tetsuya Yoshida, Nasushiobara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 0 days.

(21) Appl. No.: 13/425,777

(22) Filed: Mar. 21, 2012

(65) Prior Publication Data
US 2012/0177265 A1 Jul. 12, 2012

Related U.S. Application Data

(63) Continuation of application No. PCT/JP2011/068156, filed on Aug. 9, 2011.

(30) Foreign Application Priority Data

Aug. 11, 2010 (JP) .................................. 2010-180439

(51) Int. Cl.
*G06K 9/00* (2006.01)
(52) U.S. Cl.
USPC ............ 382/128; 382/130; 382/131; 382/162
(58) Field of Classification Search
USPC .................. 382/128, 129, 130, 131; 128/922; 250/455; 324/307, 309, 318; 600/407, 600/435, 478; 342/195
See application file for complete search history.

(56) References Cited

U.S. PATENT DOCUMENTS

| | | | |
|---|---|---|---|
| 8,472,684 B1* | 6/2013 | Periaswamy | 382/128 |
| 2002/0103437 A1 | 8/2002 | Jibiki | |
| 2008/0224700 A1* | 9/2008 | Sorensen | 324/309 |
| 2009/0136102 A1* | 5/2009 | Kimpe et al. | 382/128 |
| 2009/0198123 A1 | 8/2009 | Aoyagi et al. | |
| 2009/0299182 A1 | 12/2009 | Asafusa | |

(Continued)

FOREIGN PATENT DOCUMENTS

| | | |
|---|---|---|
| CN | 101721226 A | 6/2010 |
| JP | 2002-238901 A | 8/2002 |

(Continued)

OTHER PUBLICATIONS

International Search Report and English Translation for corresponding International Application No. PCT/JP2011/068156 mailed on Nov. 8, 2011.

(Continued)

*Primary Examiner* — Ali Bayat
(74) *Attorney, Agent, or Firm* — Yoshida & Associates, LLC

(57) ABSTRACT

An image generating unit generates a medical image. A deciding unit detects a reaching time at which a contrast agent has reached a predetermined region of the medical image. The deciding unit sets a color map in which the reaching time is associated with a hue based on a first inflow time corresponding to a first designation region set to the medical image and a second inflow time corresponding to a second designation region. A generating unit generates a hue conversion image in which a hue is allocated to each region of the medical image based on the color map and the reaching time in each region of the medical image. A control unit displays the hue conversion image through a monitor.

14 Claims, 14 Drawing Sheets

(56) References Cited

U.S. PATENT DOCUMENTS

2010/0094133 A1    4/2010    Yoshiara et al.
2010/0142786 A1*    6/2010    Degani et al. ................ 382/131

FOREIGN PATENT DOCUMENTS

| | | |
|---|---|---|
| JP | 2009-183360 A | 8/2009 |
| JP | 2010-094220 A | 4/2010 |
| JP | 2011-110211 A | 6/2011 |
| WO | 2006126684 A1 | 11/2006 |

OTHER PUBLICATIONS

Chinese Office Action with English Translation for Chinese patent Application No. 201180001964.2 mailed on Oct. 25, 2013.

* cited by examiner

FIG.14A
FIG.14B
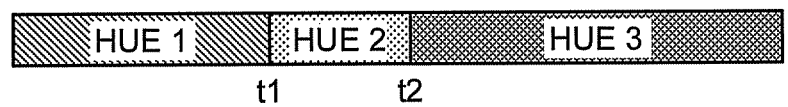
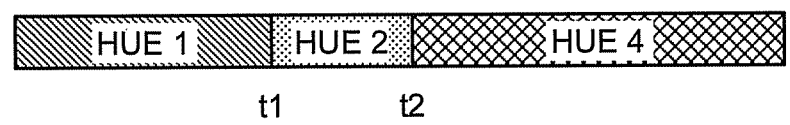

MEDICAL IMAGE DIAGNOSIS APPARATUS AND IMAGE PROCESSING APPARATUS AND METHOD

CROSS-REFERENCE TO RELATED APPLICATIONS

This application is a continuation of PCT international application Ser. No. PCT/JP2011/068156 filed on Aug. 9, 2011 which designates the United States, and which claims the benefit of priority from Japanese Patent Application No. 2010-180439, filed on Aug. 11, 2010; the entire contents of which are incorporated herein by reference.

FIELD

Embodiments described herein relate generally to a medical image diagnosis apparatus and an image processing apparatus and method.

BACKGROUND

In the related art, an ultrasonic diagnosis apparatus is relatively small in size as compared with other medical image diagnosis apparatuses such as an X-ray diagnosis apparatus, an X-ray computed tomography (CT) apparatus, and a magnetic resonance imaging (MRI) apparatus and can display the movement state of an examination target such as a heartbeat or the movement of a fetus in real time by the simple operation of making an ultrasonic probe come into contact with a body surface. Thus, the ultrasonic diagnosis apparatuses are playing play an important role in current medical care. Further, developments have been made to the size of the ultrasonic diagnosis apparatuses that have no risks of radiation exposure so that handy-held apparatuses are developed. Such an ultrasonic diagnosis apparatus can be conveniently used in medical practice such as medical care at an obstetrics office or home.

Further, an intravenous ultrasound contrast agent (hereinafter, referred to as a contrast agent) has been recently commercialized, and so a "contrast echo method" has been performed. In the contrast echo method, by enhancing a blood flow signal by injecting a micro bubble or the like as the contrast agent into a vein, blood flow moving state can be clearly observed. For example, the contrast echo method is used for an examination of organs such as the heart or the liver. A doctor can make a differential diagnosis of cancer or a diagnosis of a diffuse liver disease such as chronic hepatitis or cirrhosis with reference to the blood flow moving state visualized in an angiogram generated by the contrast echo method. For example, in the case of primary liver cancer, a doctor can make differential diagnosis as to whether a liver tumor is benign or malignant by using the blood flow information of an arterial phase and blood flow information of a portal phase visualized in an angiogram in a complementary fashion.

As a technique of clearly showing a time-dependent change in intensity of the blood flow signal for observation of the blood flow moving state by using the contrast echo method, there is a known technique of mapping the injection time of the contrast agent on a still image. For example, in the above technique, by representing a difference between peak times of a signal reflected by the contrast agent with a different hue, it is possible to clearly represent the times at which the contrast agent is injected into various portions shown on the same image.

However, in the conventional art, there has been a case in which it is difficult to discriminate the dominant regions of different vascular channels.

BRIEF DESCRIPTION OF THE DRAWINGS

FIG. 7B is a diagram for explaining an example of a hue conversion image of a patient having a diffuse liver disease or the like.

FIG. 14A is a diagram illustrating a hue conversion table generated by an ultrasonic examination of a subject P1.

FIG. 14B is a diagram illustrating a hue conversion table generated by an ultrasonic examination of a subject P2.

DETAILED DESCRIPTION

According to an embodiment, a medical image diagnosis apparatus includes an image processing unit, a time detecting unit, a color map setting unit, a generating unit, a display control unit. The image processing unit configured to generate a medical image. The time detecting unit configured to detect a reaching time at which a contrast agent has reached a predetermined region of the medical image. The color map setting unit configured to set a color map in which the reaching time is associated with a hue based on a first inflow time corresponding to a first designation region set to the medical image and a second inflow time corresponding to a second designation region. The generating unit configured to generate a hue conversion image in which a hue is allocated to each region of the medical image based on the color map and the reaching time in each region of the medical image. The display control unit configured to display the hue conversion image through a predetermined display unit.

(First Embodiment)

Figure 1:
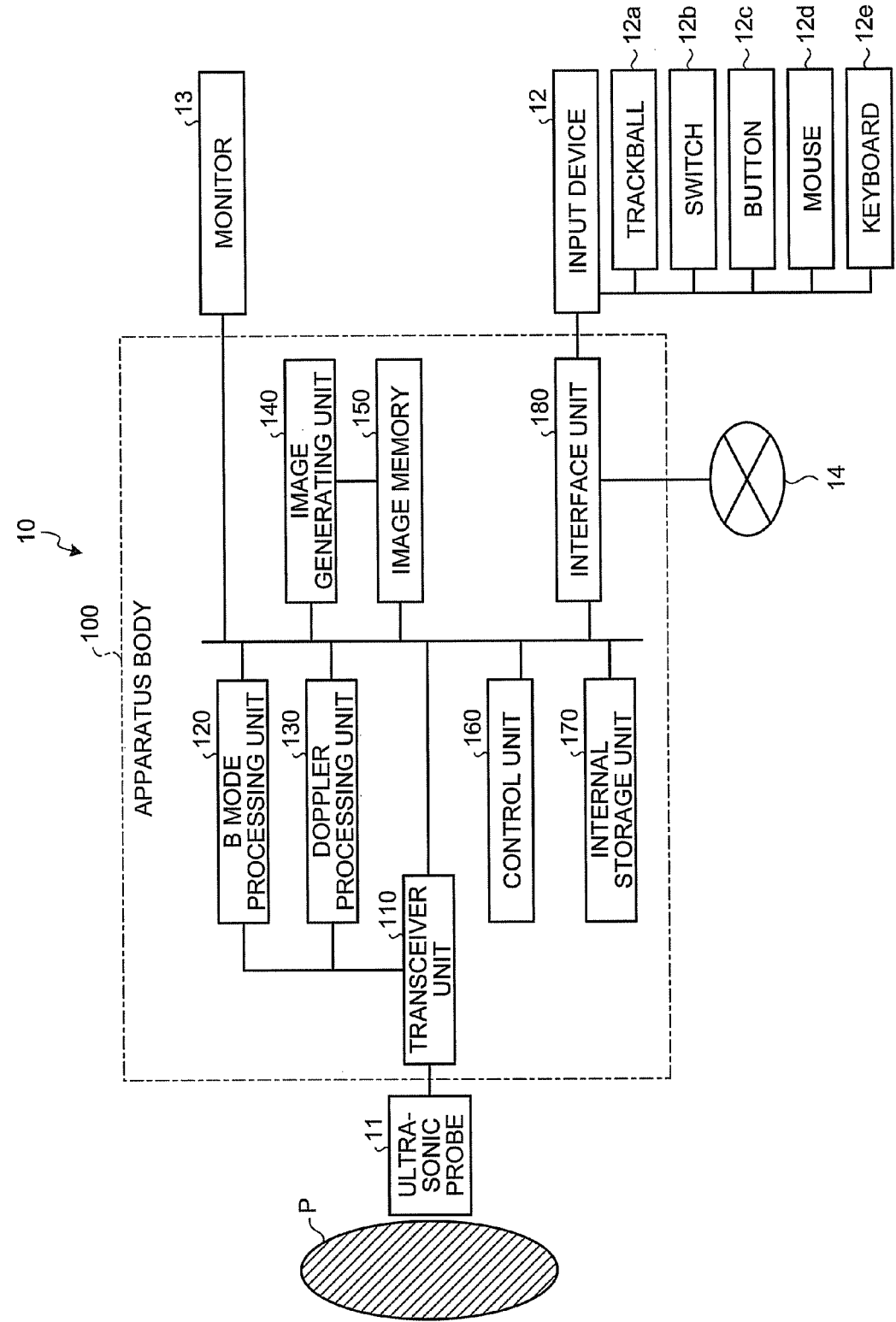
FIG. 1 is a diagram for explaining the configuration of an ultrasonic diagnosis apparatus according to a first embodiment.

First, a configuration of an ultrasonic diagnosis apparatus according to a first embodiment will be described with reference to FIG. 1. FIG. 1 is a diagram for explaining the configuration of an ultrasonic diagnosis apparatus 10 according to the first embodiment. As illustrated in FIG. 1, the ultrasonic diagnosis apparatus 10 according to the first embodiment includes an ultrasonic probe 11, an input device 12, a monitor 13, and an apparatus body 100. The ultrasonic diagnosis apparatus 10 is connected to a network 14.

The ultrasonic probe 11 includes a plurality of piezoelectric elements. The plurality of piezoelectric elements generate an ultrasonic wave based on a driving signal supplied from a transceiver unit 110 included in the apparatus body 100 which will be described later, the piezoelectric elements receive the reflective wave from a subject P, and convert the reflective wave into an electrical signal. The ultrasonic probe 11 includes a matching layer disposed in the piezoelectric element and a backing material for preventing the ultrasonic wave from propagating backward from the piezoelectric element.

When the ultrasonic wave is transmitted from the ultrasonic probe 11 to the subject P, the transmitted ultrasonic wave is sequentially reflected against a discontinuous surface of acoustic impedance in the body tissue of the subject P and received by the plurality of piezoelectric elements included in the ultrasonic probe 11 as a reflective wave signal. The amplitude of the received reflective wave signal depends on the difference of the acoustic impedance in the discontinuous surface against which the ultrasonic wave is reflected. When the transmitted ultrasonic pulse is reflected against a moving blood flow or a surface such as a heart wall, the reflective wave signal is frequency-shifted depending on a velocity component of a moving body in an ultrasonic wave transmission direction due to the Doppler effect.

The present embodiment can be applied even when the subject P is two-dimensionally scanned by the ultrasonic probe 11 that is a one-dimensional ultrasonic probe in which a plurality of piezoelectric vibrators are arranged in a row. The present embodiment can be also applied even when the subject P is three-dimensionally scanned by the ultrasonic probe 11 that mechanically vibrates a plurality of piezoelectric vibrators of a one-dimensional ultrasonic probe or the ultrasonic probe 11 that is a two-dimensional ultrasonic probe in which a plurality of piezoelectric vibrators are two-dimensionally arranged in a lattice form.

The input device 12 includes a trackball 12a, a switch 12b, a button 12c, a mouse 12d, a keyboard 12e, and the like. The input device 12 receives various setting requests from an operator of the ultrasonic diagnosis apparatus 10 and transmits the received various setting requests (for example, a region-of-interest setting request, an image quality condition setting instruction, or the like) to the apparatus body 100.

The monitor 13 displays a graphical user interface (GUI) that allows the operator of the ultrasonic diagnosis apparatus 10 to input various setting requests through the input device 12 or displays an ultrasonic image or the like generated in the apparatus body 100.

The apparatus body 100 generates the ultrasonic image based on the reflective wave received by the ultrasonic probe 11. The apparatus body 100 includes the transceiver unit 110, a B mode processing unit 120, a Doppler processing unit 130, an image generating unit 140, an image memory 150, a control unit 160, an internal storage unit 170, and an interface unit 180 as illustrated in FIG. 1.

The transceiver unit 110 includes a trigger generating circuit, a delay circuit, a pulsar circuit, and the like and supplies the ultrasonic probe 11 with a driving signal. The pulsar circuit repetitively generates a pulse rate for forming a transmission ultrasonic wave at a predetermined rate frequency. The delay circuit applies a delay time of each piezoelectric vibrator necessary for focusing the ultrasonic wave generated from the ultrasonic probe 11 in a beam form and deciding the transmission directivity to each pulse rate generated by the pulsar circuit. The trigger circuit applies the driving signal (a driving pulse) to the ultrasonic probe 11 at the timing based on the pulse rate. That is, by changing the delay time applied to each pulse rate, the delay circuit arbitrarily adjusts the transmission direction from the piezoelectric vibrator surface.

The transceiver unit 110 includes an amplifier circuit, an analog/digital (A/D) converter, an adder, and the like. The transceiver unit 110 performs various processes on the reflective wave signal received by the ultrasonic probe 11 and generates reflective wave data. The amplifier circuit amplifies the reflective wave signal for each channel and performs a gain correction process. The A/D converter performs A/D conversion on the gain-corrected reflective wave signal and applies the delay time necessary for deciding reception directivity. The adder performs an addition process on the reflective wave signal processed by the A/D converter and generates the reflective wave data. A reflective component of the reflective wave signal from a direction according to the reception directivity is emphasized by the addition process of the adder.

As described above, the transceiver unit 110 controls the transmission directivity and the reception directivity for transmission and reception of the ultrasonic wave. The transceiver unit 110 has a function capable of instantaneously changing delay information, a transmission frequency, a transmission driving voltage, the number of opening elements, or the like by control of the control unit 160 which will be described later. Particularly, the transmission driving voltage is changed by an oscillating circuit of a linear amplifier type capable of instantaneously switching a value or a mechanism of electrically switching a plurality of power supply units. Further, the transceiver unit 110 can transmit and receive different waveforms at one frame or one rate intervals.

The B mode processing unit 120 receives the reflective wave data, which is the processed reflective wave signal that has been subjected to the gain correction process, the A/D conversion process, and the addition process, from the transceiver unit 110. Then, the B mode processing unit 120 performs logarithmic amplification, an envelope detection process, and the like and so generates data (B mode data) representing the signal intensity using a level of brightness.

Here, the B mode processing unit 120 can change a frequency band for imaging by changing the detection frequency. Further, the B mode processing unit 120 can perform detection processes by two detection frequencies on one reception data in parallel.

Using the function of the B mode processing unit 120, it is possible to separate the reflective wave data having an ultrasonic contrast agent (micro bubble) flowing through a region of interest as a reflection source and the reflective wave data having tissue present in the region of interest as a reflection source from one reception data in the region of interest of the subject P into which the ultrasonic contrast agent is injected.

The image generating unit 140 which will be described later can generate an angiogram in which a flowing bubble is imaged with high sensitivity and a histological image in which tissue is imaged to observe its form.

Here, the angiogram is usually generated mainly based on a second harmonic (second-order high frequency) component that is a non-linear signal, and the histological image for observing the form is generated mainly based on a fundamental wave component. Hereinafter, the B mode data of the second harmonic component which the B mode processing unit 120 separates from the reception data so as to generate the angiogram is referred to as a "signal 1", and the B mode data of the fundamental wave component which the B mode processing unit 120 separates from the reception data so as to generate the histological image is referred to as a "signal 2".

The Doppler processing unit 130 performs a frequency analysis on velocity information based on the reflective wave data received from the transceiver unit 110, extracts a blood flow, tissue, a contrast agent echo component by the Doppler effect, and generates data (Doppler data) obtained by extracting moving body information such as average velocity, a dispersion, or power at multiple points.

The image generating unit 140 generates an ultrasonic image based on the B mode data generated by the B mode processing unit 120 or the Doppler data generated by the Doppler processing unit 130. Specifically, the image generating unit 140 generates the ultrasonic image (the B mode image or the Doppler image) to display based on the B mode data or the Doppler data by converting (scan converter) a scanning line signal string of an ultrasonic scan into a scanning line signal string of a video format represented by a television or the like. Further, the image generating unit 140 generates a hue conversion image in which the angiogram is color-mapped based on the B mode data (signal 1) of the second harmonic component separated from the reception data by the B mode processing unit 120. The generation of the hue conversion image will be described later.

The image memory 150 stores image data, such as the angiogram and the histological image generated by the image generating unit 140. The image memory 150 stores the processing result by the image generating unit 140 which will be described later. Further, the image memory 150 stores an output signal (a radio frequency (RF)) directly after passing through the transceiver unit 110, a brightness signal of an image, a variety of raw data, the image data acquired through the network 14, and the like as necessary. The image data stored in the image memory 150 may have a data format which has been converted into a video format to be displayed on the monitor 13 by the control unit 160 which will be described later or a data format of raw data which has not been subjected to coordinate conversion.

The control unit 160 controls the entire process in the ultrasonic diagnosis apparatus 10. Specifically, the control unit 160 controls the processes of the transceiver unit 110, the B mode processing unit 120, the Doppler processing unit 130, and the image generating unit 140 based on various setting requests which the operator has input through the input device 12, various control programs read from the internal storage unit 170, or various pieces of setting information. The control unit 160 also performs the control such that the ultrasonic image stored in the image memory 150 or the like is displayed on the monitor 13.

The internal storage unit 170 stores various data such as the control programs for performing transmission and reception of the ultrasonic wave, an image processing, and a display process, diagnosis information (for example, a patient ID, a doctor's comment, and the like), a diagnosis protocol, a body mark, or various setting information. Moreover, the internal storage unit 170 is also used for the storage of an image stored in the image memory 150 as necessary.

The interface unit 180 is an interface for controlling the exchange of various pieces of information among the input device 12, the network 14, and the apparatus body 100. For example, the interface unit 180 controls the transmission of data stored in the image memory 150 or the internal storage unit 170 to another apparatus on the network 14.

As described above, the ultrasonic diagnosis apparatus 10 according to the first embodiment generates the angiogram or the histological image based on the reflective wave of the ultrasonic wave transmitted from the ultrasonic probe 11. The ultrasonic diagnosis apparatus 10 according to the first embodiment images dominant regions of different vascular channels by a simple operation through a process of the image generating unit 140 which will be described later, so that the dominant regions of the different vascular channels can be easily discriminated. Specifically, in the subject P dosed with the contrast agent, the image generating unit 140 according to the first embodiment images a dominant region of a vascular channel into which the contrast agent flows fast and the dominant region of a vascular channel into which the contrast agent flows slowly with different hues. As a result, the dominant regions of the different vascular channels can be easily discriminated by the ultrasonic diagnosis apparatus 10 according to the first embodiment.

The process of the image generating unit 140 according to the first embodiment will be described in detail with reference to FIG. 2 and the like. Here, in the first embodiment, the process is performed on each of a plurality of angiograms sequentially generated by irradiating the subject P dosed with the contrast agent with the ultrasonic wave and extracting the second harmonic component based on the reflective wave. The present process may be performed each time when the angiogram is generated or may be performed after the angiogram is completely generated. The first embodiment is described in connection with a case in which dominant regions (liver parenchyma) of the portal vein and the artery in the liver of the subject P are imaged with different hues. It is known that the contrast agent flows into the portal vein slowly compared to the artery.

Figure 2:
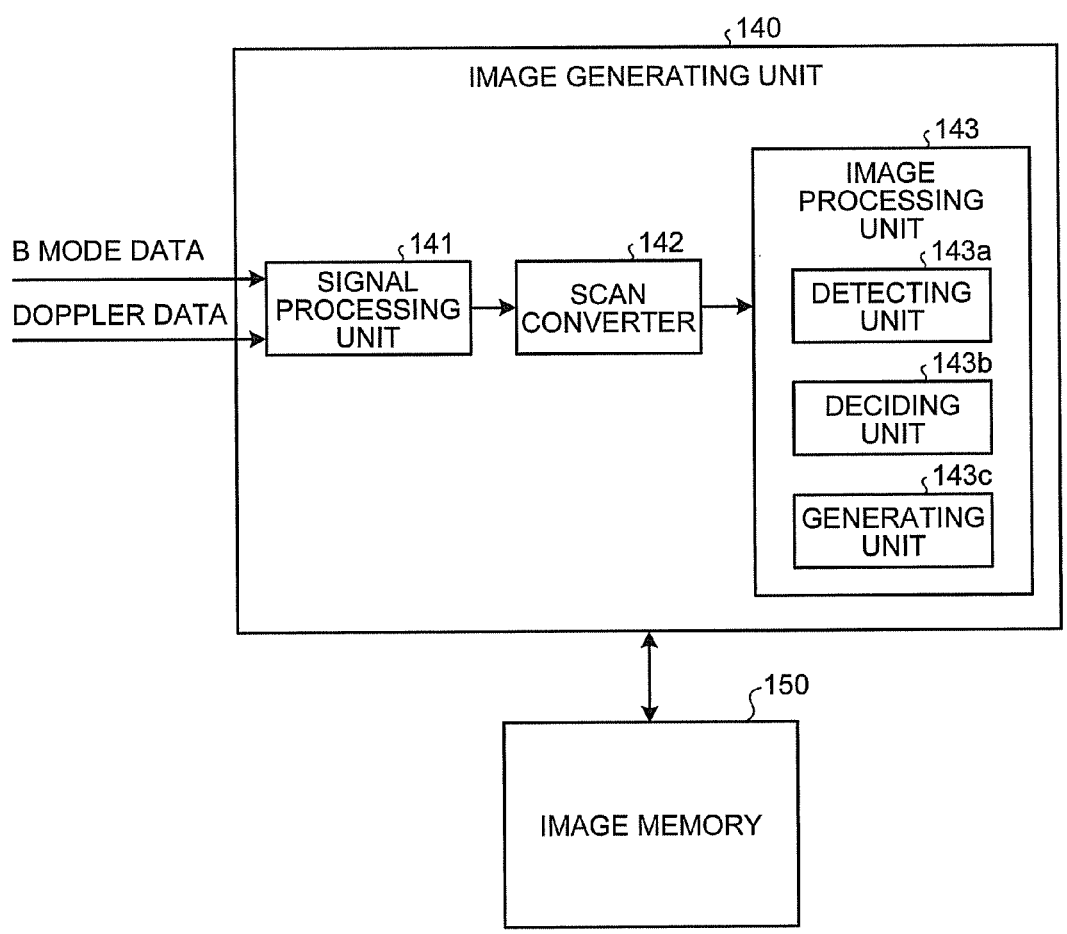
FIG. 2 is a diagram for explaining a configuration of an image generating unit according to the first embodiment.

FIG. 2 is a diagram for explaining the configuration of the image generating unit 140 according to the first embodiment. The image generating unit 140 according to the first embodiment includes a signal processing unit 141, a scan converter 142, and an image processing unit 143 as illustrated in FIG. 2.

The signal processing unit 141 executes a filtering process on the B mode data and the Doppler data. Specifically, the signal processing unit 141 removes the noise component from the ultrasonic scan scanning line signal string. The scan converter 142 converts the ultrasonic scan scanning line signal string of data such as the received brightness data or blood flow information into a scanning line signal string of a general video format of a television or the like.

The image processing unit 143 includes a detecting unit 143a, a deciding unit 143b, and a generating unit 143c as illustrated in FIG. 2 and generates the hue conversion image in which the angiogram is color-mapped. The detecting unit 143a detects intensity of the reflective wave signal in the angiogram that is the ultrasonic image generated by the reflective wave signal of the ultrasonic wave caused by the contrast agent. Specifically, the detecting unit 143a uses the brightness of pixels of the angiogram as the intensity of the reflective wave signal. For example, the detecting unit 143a detects the brightness of the angiogram generated by the scan converter 142 based on the B mode data generated by the B mode processing unit 120.

The deciding unit 143b decides a reaching time, at which the intensity of the reflective wave signal detected by the detecting unit 143a has reached a predetermined threshold value, on each of a plurality of regions of interest of the angiogram. Specifically, the deciding unit 143b decides a time at which the ratio of the number of pixels whose brightness has reached a predetermined brightness among the pixels configuring the regions of interest has exceeded a predetermined threshold value as the reaching time. Alternatively, the deciding unit 143b decides a time at which the average brightness that is an average of the brightness of pixels configuring the regions of interest has exceeded a predetermined threshold value as the reaching time.

Figure 3:
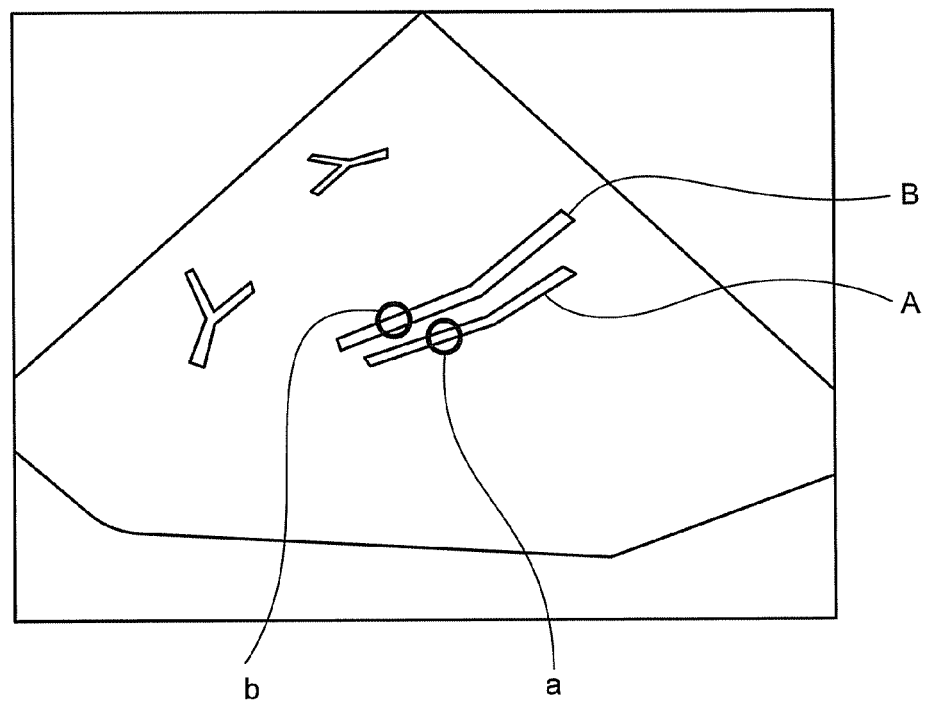
FIG. 3 is a diagram for explaining an example of a region of interest according to the first embodiment.

Here, the region of interest (ROI) will be first described. The region of interest refers to a region designated by the operator of the ultrasonic diagnosis apparatus 10, a doctor, or the like and includes a vascular channel. FIG. 3 is a diagram for explaining the region of interest according to the first embodiment.

FIG. 3 illustrates an angiogram of the liver that is the subject P dosed with the contrast agent, the liver parenchyma and vascular channels are shown. For example, the operator of the ultrasonic diagnosis apparatus 10, the doctor, or the like designates a region a of interest and a region b of interest in a vascular channel A and a vascular channel B, respectively as illustrated in FIG. 3. For example, the vascular channel A is the hepatic artery, and the vascular channel B is the portal vein. As an image in which the region of interest is designated, there may be used any one of a plurality of angiograms obtained at the time of ultrasonic examination of the subject P or the histological image may be used.

Figure 4:
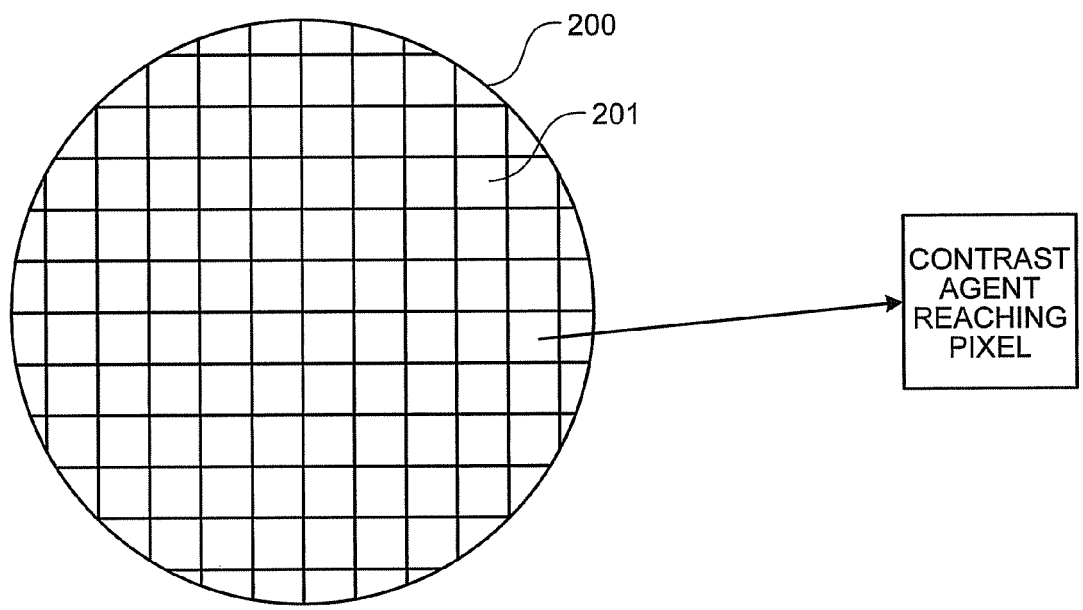
FIG. 4 is a diagram for explaining an example of detecting the brightness in a region of interest.

When the region of interest is designated by the operator of the ultrasonic diagnosis apparatus 10, the doctor, or the like as illustrated in FIG. 3, the deciding unit 143b decides the reaching time at which the ratio of the number of pixels whose brightness detected by the detecting unit 143a has reached a predetermined brightness, among the pixels constituting the region of interest, exceeds a predetermined threshold value. Here, the detection of brightness by the detecting unit 143a will be first described. FIG. 4 is a diagram for explaining an example of detecting the brightness in the region of interest.

FIG. 4 illustrates the detection of brightness of the regions of interest designated by the doctor or the like such as the region a of interest and the region b of interest illustrated in FIG. 3. For example, the detecting unit 143a detects the brightness of each pixel 201 included in a region 200 of interest as illustrated in FIG. 4. The detecting unit 143a detects the brightness of each pixel 201 included in the region of interest in time-series order on all frames designated by the operator, the doctor, or the like in a plurality of angiograms obtained at the time of ultrasonic examination of the subject P.

Then, the deciding unit 143b determines whether or not the brightness of each pixel 201 detected by the detecting unit 143a for each frame in time-series order has reached a threshold value as illustrated in FIG. 4. When the brightness has reached the threshold value, the deciding unit 143b decides the corresponding pixel 201 as a contrast agent reaching pixel that is a pixel that the contrast agent has reached as illustrated in FIG. 4. Then, the deciding unit 143b decides whether or not a ratio of the contrast agent reaching pixels to all pixels 201 in the region 200 of interest has reached a predetermined threshold value. Here, when the ratio of the contrast agent reaching pixels to all pixels 201 in the region 200 of interest has reached a predetermined threshold value, the deciding unit 143b determines that the contrast agent has reached the corresponding region 200 of interest and decides a reaching time. That is, the deciding unit 143b decides a time at which the contrast agent has reached the vascular channel within the region 200 of interest.

Figure 5:
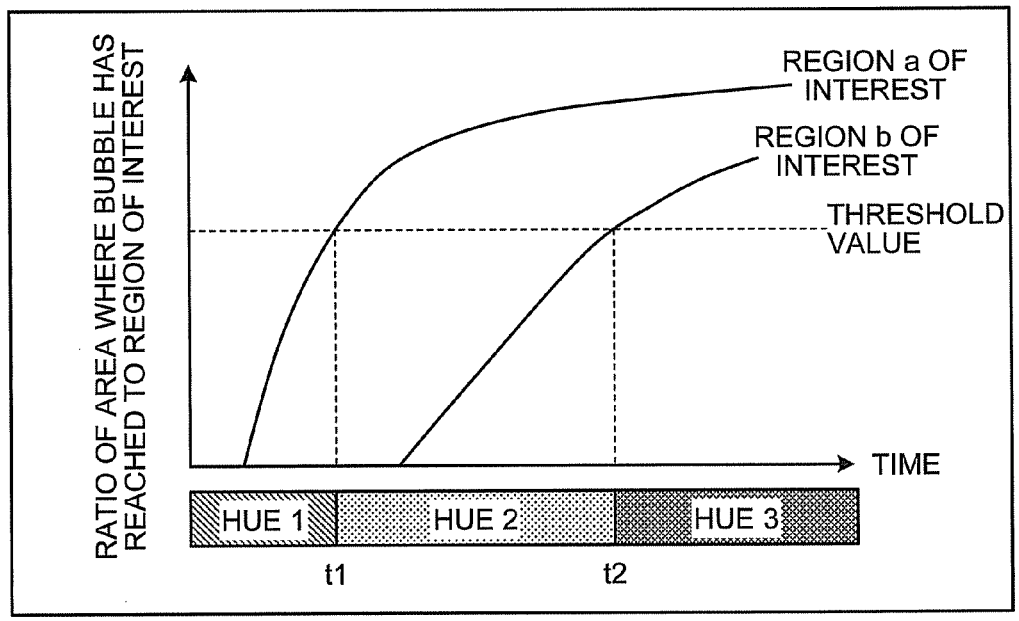
FIG. 5 is a diagram for explaining an example of deciding a contrast agent reaching time.

FIG. 5 is a diagram for explaining an example of decoding the contrast agent reaching time. In FIG. 5, the horizontal axis represents time, and the vertical axis represents the ratio that the contrast agent (bubble) has reached within the region of interest. Further, FIG. 5 illustrates an example of determining whether or not the contrast agent has reached the region a of interest and the region b of interest illustrated in FIG. 3. For example, the deciding unit 143b decides the time t1 at which the ratio of the contrast agent reaching pixels to all pixels included in the region a of interest has reached the threshold value as illustrated in FIG. 5. That is, the time refers to a time of a frame in which arrival of the contrast agent at the vascular channel designated as the region of interest in a plurality of angiograms is imaged.

Similarly, the deciding unit 143b decides the time t2 at which the ratio of the contrast agent reaching pixels to all pixels included in the region b of interest has reached the threshold value as illustrated in FIG. 5. Here, as illustrated in FIG. 5, a hue 1 is previously set as a hue until the reaching time t1 comes, a hue 2 is previously set as a hue between the reaching time t1 and the reaching time t2, and a hue 3 is previously set as a hue after the arrival time t2 elapses. The decision of the contrast agent reaching pixel has been described in connection with the case in which the pixel included in the region of interest is decided as the contrast agent reaching pixel when the brightness of the corresponding pixel has reached a predetermined threshold value. However, the present embodiment is not limited thereto. For example, when brightness of the pixel becomes the maximum, the corresponding pixel may be decided as the contrast agent arrival pixel. Further, the decision of the contrast agent reaching pixel has been described in connection with the case of using whether or not the ratio of the contrast agent reaching pixels to all pixels included in the region of interest has reached a predetermined threshold value. However, the present embodiment is not limited thereto. For example, when the average brightness that is the average of brightness of all pixels included in the region of interest reaches the maximum value or exceeds an arbitrary value, it may be decided that the contrast agent has reached the region of interest.

Returning to FIG. 2, after the new arrival time has been decided by the deciding unit 143b, the generating unit 143c generates a hue conversion image in which regions having reached a predetermined threshold value at different reaching times are represented by different hues by changing a hue allocated to a region having reached the predetermined threshold value. Further, the generating unit 143c further generates a hue conversion table in which hues allocated in the hue conversion image are represented along a time axis.

Specifically, in a plurality of angiograms of the angiogram of the subject P, the generating unit 143c generates the hue conversion image in which regions, where the reflecting wave signal by the contrast agent has been detected between the reaching time of the contrast agent in one region of interest and the reaching time of the contrast agent in another region of interest, are represented by the same hue. Further, the generating unit 143c generates the hue conversion table in which the hue changes at the reaching time of the contrast agent decided by the deciding unit 143b. Then, the generating unit 143c stores the generated hue conversion image and the hue conversion table in the image memory 150.

Figure 6:
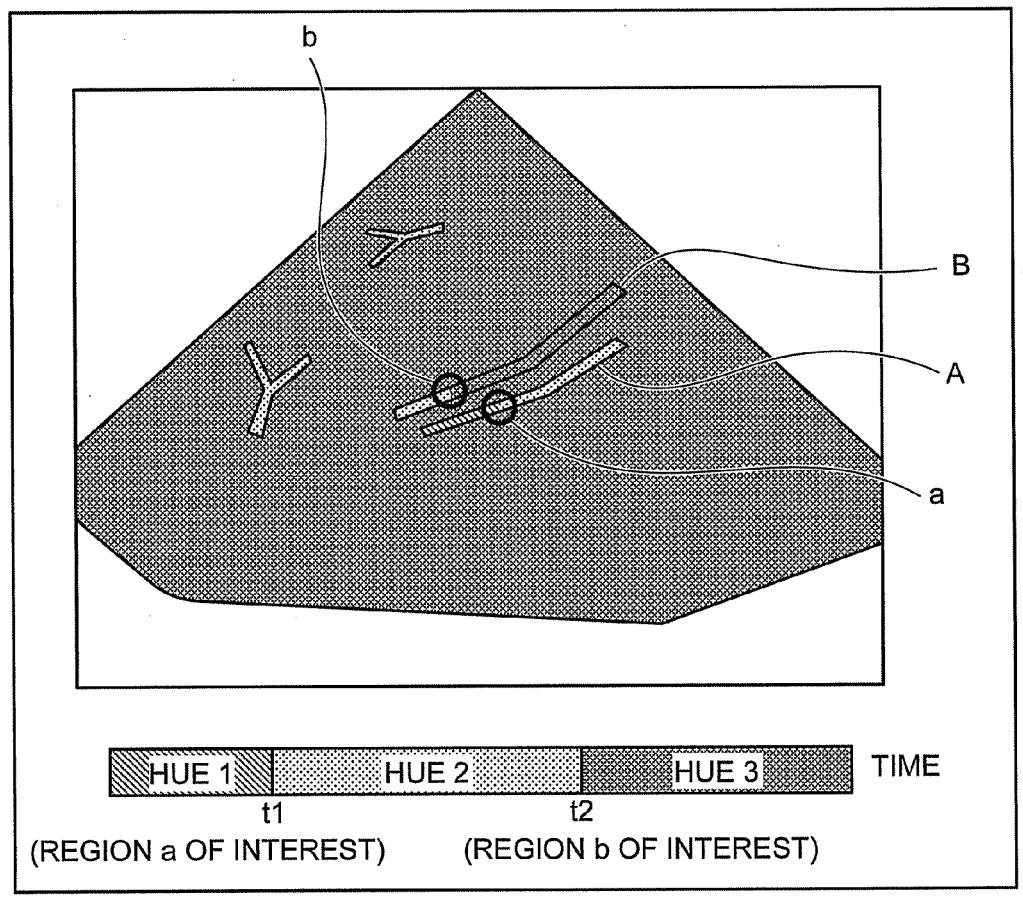
FIG. 6 is a diagram for explaining an example of a hue conversion image.

FIG. 6 is a diagram for explaining an example of the hue conversion image. FIG. 6 illustrates the hue conversion image and the hue conversion table of the angiogram illustrated in FIG. 3. For example, the generating unit 143c generates a hue conversion image in which a time before the contrast agent reaches the region a of interest is represented by the hue 1, a time between the reaching time t1 of the contrast agent on the region a of interest and the reaching time t2 of the contrast agent on the region b of interest is represented by the hue 2, and a time after the reaching time t2 is represented by the hue 3 as illustrated in FIG. 6. The generating unit 143c generates a hue conversion table in which the hue 1 is changed to the hue 2 at the reaching time t1 of the contrast agent on the region a of interest, and the hue 2 is changed to the hue 3 at the reaching time t2 of the contrast agent on the region b of interest as illustrated in FIG. 6.

That is, a region represented by the hue 2 in FIG. 6 is a region which the contrast agent has reached between the reaching time t1 and the reaching time t2. Further, a region represented by the hue 3 in FIG. 6 is a region at which the contrast agent has reached after the reaching time t2. It can be understood from FIG. 6 that the liver parenchyma illustrated in FIG. 6 is dominated (nourished) by the vascular channel B.

FIG. 6 illustrates the hue conversion image in which color mapping has been performed using all of angiograms generated before a time of a certain frame. However, the hue conversion image is actually updated and generated for each of all frames. Thus, when all of the hue conversion images are stored and viewed as a moving picture, the state in which the contrast agent flows into the liver of the subject P and so brightness gradually changes can be vividly seen due to the hues. Through the moving picture, it is possible to see the hue conversion image whose hue changes each time when the contrast agent reaches the region of interest.

The generating unit 143c generates a hue conversion image after correcting the deviation between the angiograms used for generating the hue conversion image. Specifically, the generating unit 143c generates a hue conversion image in which the positional deviation between frames occurring when the subject P moves or when the ultrasonic probe 11 is shaken has been corrected.

For example, the generating unit 143c extracts feature points of the angiogram included in frames and corrects the positional deviation between frames based on the extracted feature points. Then, the generating unit 143c generates the hue conversion image based on the angiogram whose position deviation between the frames has been corrected.

Figure 7A:
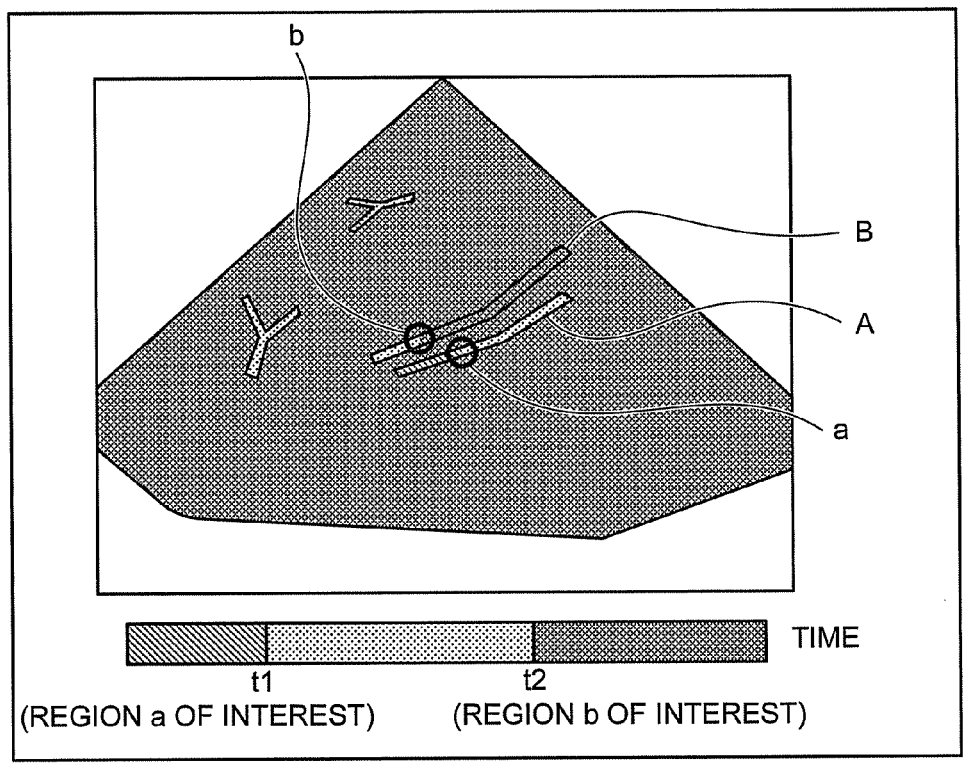
FIG. 7A is a diagram for explaining an example of a hue conversion image of a healthy person.
Figure 7B:
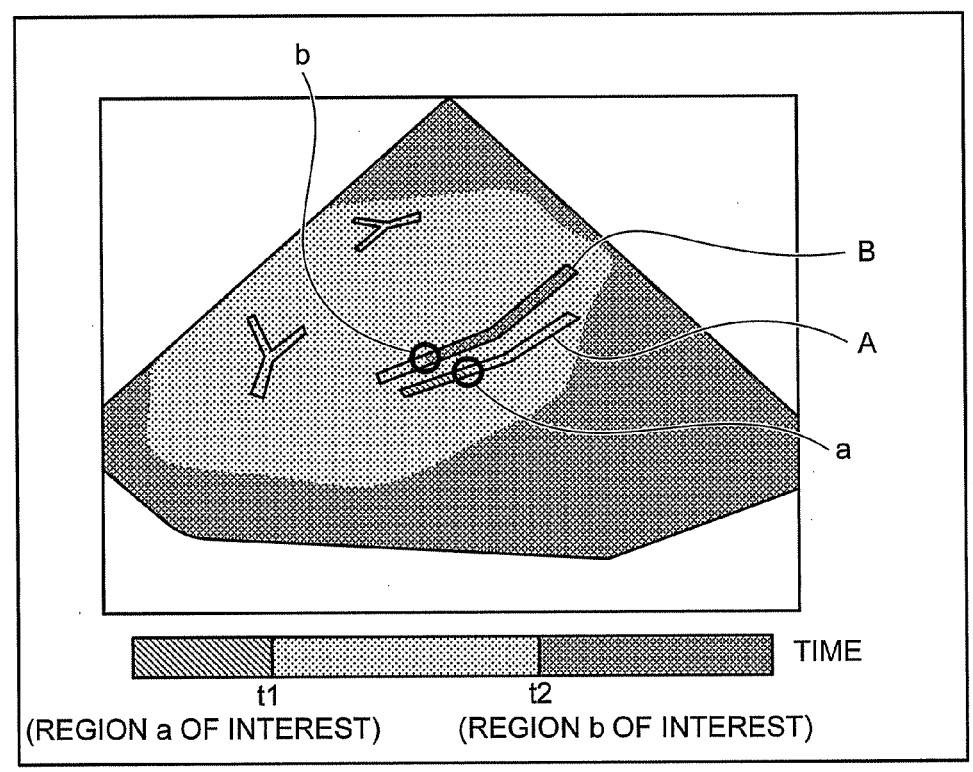

Here, a description will be made in connection with an example of using the ultrasonic diagnosis apparatus 10 according to the first embodiment. For example, when an ultrasonic examination using the ultrasonic diagnosis apparatus 10 according to the first embodiment is executed on a patient having a diffuse liver disease or the like, a change in the blood flow moving state is shown in the hue conversion image. An example of the change in the blood flow moving state will be described below with reference to FIGS. 7A and 7B. FIG. 7A is a diagram for explaining an example of a hue conversion image of a healthy person. FIG. 7B is a diagram for explaining an example of a hue conversion image of a patient having a diffuse liver disease or the like.

As illustrated in FIG. 7A, the liver parenchyma, of the liver of the healthy person, is dominated by the vascular channel B. Meanwhile, in the liver of the patient who has a diffuse liver disease or the like, as illustrated in FIG. 7B, the hue 2 represents the region of the liver parenchyma dominated by the vascular channel A which the contrast agent has reached between the reaching time t1 and the reaching time t2, and it is apparent that the blood flow moving state changes and the region of the liver parenchyma which is dominated by the vascular channel A is increasing. That is, provided is an image that is easy for the operator of the ultrasonic diagnosis apparatus 10, the doctor, or the like to recognize the change in the blood flow moving state.

Figure 8A:
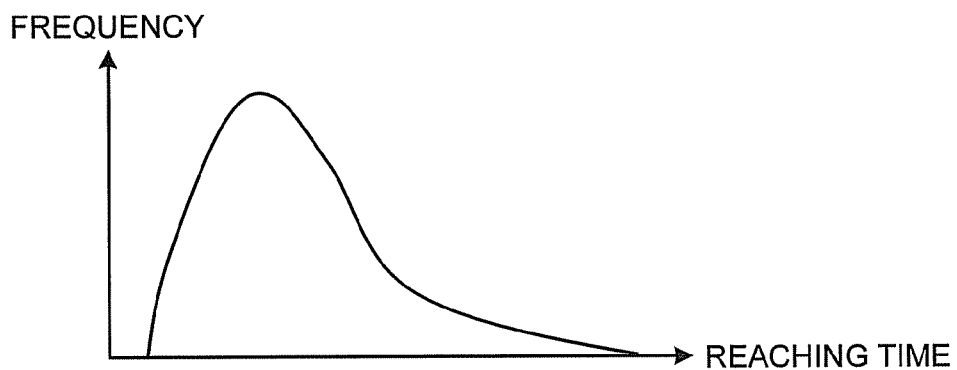
FIG. 8A is a diagram illustrating an example of a frequency distribution of a reaching time.
Figure 8B:
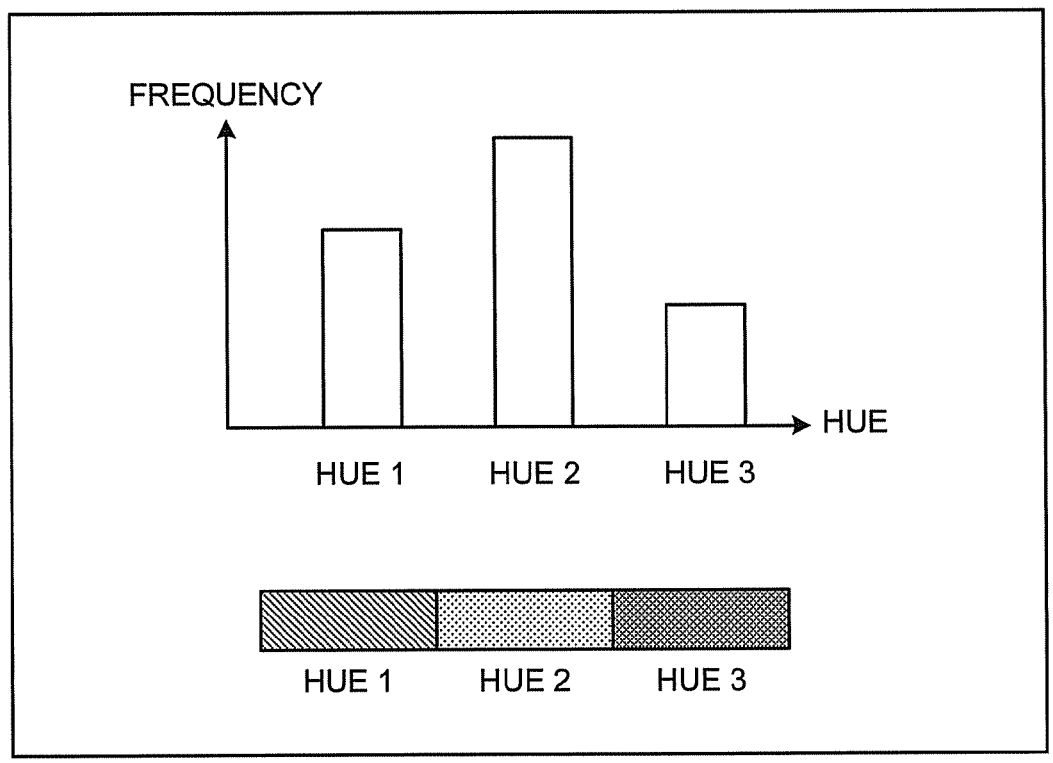
FIG. 8B is a diagram illustrating an example of a frequency distribution of hues.

The generating unit 143c generates a frequency distribution in which the time at which the intensity of the reflective wave signal in each of the pixels included in the angiogram or the region of interest have reached the predetermined threshold value or a hue on a hue conversion image is associated with the number of pixels and stores the frequency distribution in the image memory 150. FIG. 8A is a diagram illustrating an example of the frequency distribution of the reaching times. FIG. 8B is a diagram illustrating an example of the frequency distribution of each hue.

For example, the generating unit 143c generates a diagram representing the frequency distribution of pixels for each reaching time as illustrated in FIG. 8A. Further, the generating unit 143c generates a histogram representing the frequency of pixels for each hue as illustrated in FIG. 8B. The generating unit 143c can calculate a mode value (peak), a gravity center, a dispersion, and the like of the histogram as illustrated in FIGS. 8A and 8B.

As described above, the control unit 160 reads the hue conversion image and the hue conversion table generated by the image generating unit 140 out of the image memory 150 and displays the hue conversion image and the hue conversion table on the monitor 13. As a result, in the ultrasonic diagnosis apparatus 10 according to the first embodiment, dominant regions of different vascular channels can be imaged by different hues, and thus dominant regions of different vascular channels can be easily discriminated.

Figure 9:
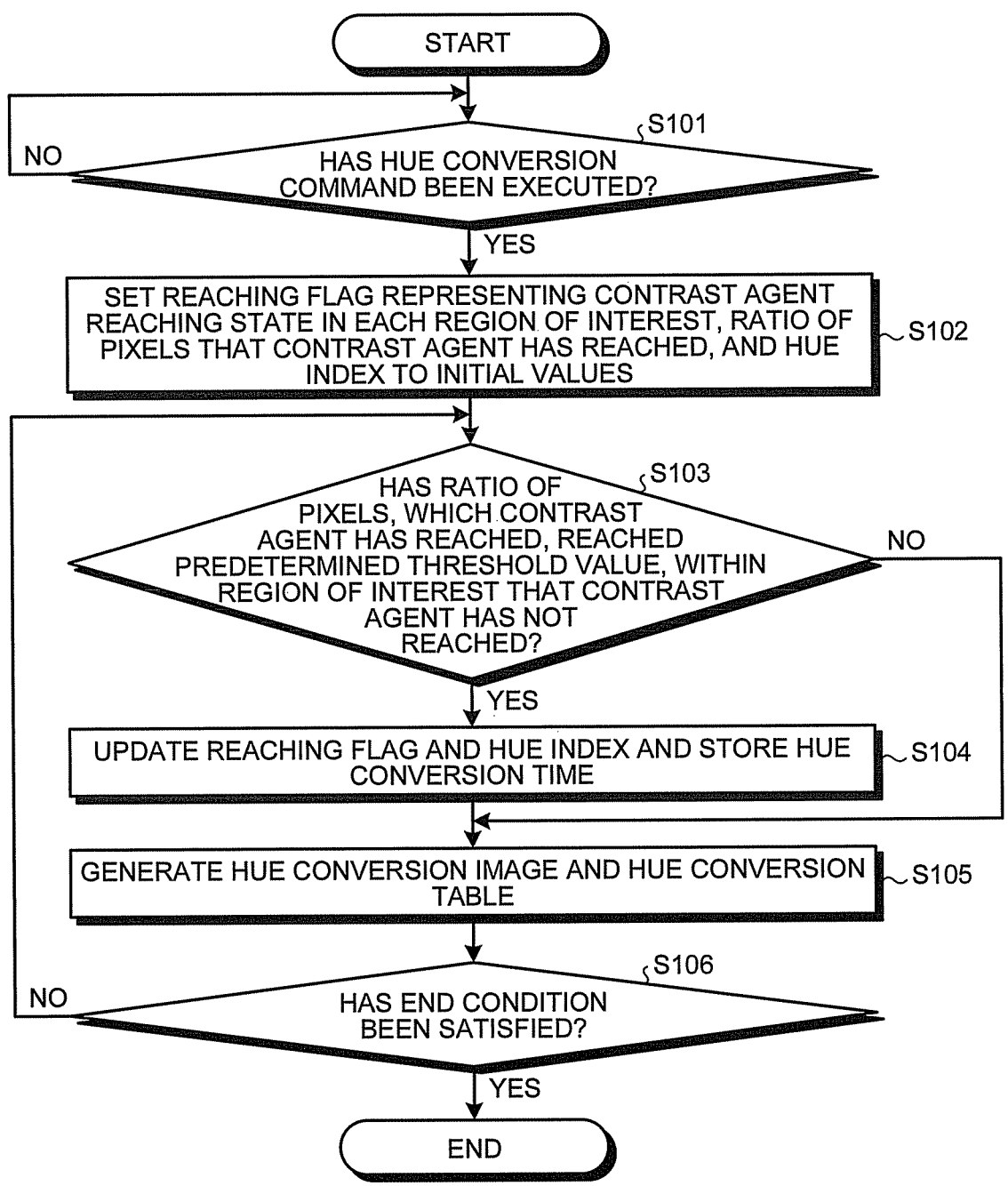
FIG. 9 is a flowchart illustrating a procedure of a process performed by the ultrasonic diagnosis apparatus according to the first embodiment.

Next, a description will be made in connection with a process of the ultrasonic diagnosis apparatus 10 according to the first embodiment. FIG. 9 is a flowchart illustrating a procedure of the process performed by the ultrasonic diagnosis apparatus 10 according to the first embodiment. In particular, FIG. 9 illustrates the process after the operator, the doctor, or the like has designated the region of interest in the angiogram of the subject P. As illustrated in FIG. 9, in the ultrasonic diagnosis apparatus 10 according to the first embodiment, when a hue conversion command is executed (Yes in step S101), the deciding unit 143b sets a flag representing the contrast agent reaching state in each region of interest, a ratio of pixels which the contrast agent has reached, and a hue index to initial values (step S102).

Then, the detecting unit 143a detects the brightness of each pixel included in each region of interest, and the deciding unit 143b determines, within the region of interest where the contrast agent has not reached, whether or not the ratio of pixels, which indicates the contrast agent having reached, has reached the predetermined threshold value (step S103). Here, when the ratio of pixels indicating the contrast agent having reached becomes the predetermined threshold value (Yes in step S103), the deciding unit 143b updates the reaching flag and the hue index and stores a hue conversion time in the image memory 150 (step S104). Then, the generating unit 143c generates the hue conversion image and the hue conversion table with reference to the hue index and the hue conversion time stored in the image memory 150 (step S105).

Meanwhile, when it is determined in step S103 that the ratio of pixels which the contrast agent has reached has not reached the predetermined threshold value (No in step S103), the generating unit 143c generates the hue conversion image and the hue conversion table (step S105). That is, the generating unit 143c generates the hue conversion image and the hue conversion table with reference to the non-updated hue index stored in the image memory 150.

Then, the generating unit 143c determines whether or not the end condition has been satisfied (step S106). Here, when the end condition has not been satisfied (No in step S106), the process returns to step S103, and the deciding unit 143b determines, within the region of interest where the contrast agent has not reached, whether or not the ratio of pixels indicating the contrast agent having reached becomes a predetermined threshold value. However, when the end condition has been satisfied (Yes in step S106), the ultrasonic diagnosis apparatus 10 finishes the process. The end condition in step S106 may be satisfied when all the frames designated by the operator, the doctor, or the like have been processed.

As described above, according to the first embodiment, the detecting unit 143a detects the intensity of the reflective wave signal in the angiogram that is the ultrasonic image generated by the reflective wave signal of the ultrasonic wave caused by the contrast agent. Then, the deciding unit 143b decides the reaching times in which the intensity of the reflective wave signal detected by the detecting unit 143a has reached a predetermined threshold value in each of the plurality of regions of interest of the angiogram. Then, after the new reaching time is decided by the deciding unit 143b, by changing the hue allocated to the region in which the intensity of the reflective wave signal has reached the predetermined threshold value, the generating unit 143c generates the hue conversion image in which the regions having reached the predetermined threshold value at different reaching times are represented by different hues. The control unit 160 displays the hue conversion image generated by the generating unit 143c through the monitor 13. Thus, the ultrasonic diagnosis apparatus 10 according to the first embodiment can image the dominant regions of the different vascular channels by different hues, so that the dominant regions of different vascular channels can be easily discriminated.

According to the first embodiment, the generating unit 143c further generates the hue conversion table in which hues allocated to the hue conversion image are represented along the time axis. The control unit 160 further displays the hue conversion table through the monitor 13. Thus, the ultrasonic diagnosis apparatus 10 according to the first embodiment can make a clear relation between an inflow time of the contrast agent and the hue.

For example, there is a known technique of separating the artery from the portal vein so that inflow times of the contrast agent into different vascular channels are recognized in advance and then the artery and the portal vein are represented by different hues. Further, there is a technique of discriminating another dominant region so that the contrast agent is prevented from flowing into the dominant region of a certain vascular channel by destroying the contrast agent flowing through a certain vascular channel by irradiation of a high-sound pressure ultrasonic wave, and thus the brightness of the dominant region in the angiogram is lowered. However, in the technique of separating the artery from the portal vein, it is necessary to know the type or the degree of a disease and the inflow time of the contrast agent of each patient in advance, and so time and effort are required until an ultrasonic examination is performed. Further, in the technique of discriminating another dominant region by lowering the brightness of the dominant region in the angiogram, it is difficult to set an irradiation cross section or the like since only a certain vascular channel has to be selectively irradiated with the high-sound pressure ultrasonic wave.

In the ultrasonic diagnosis apparatus 10 according to the present embodiment, the operator or the doctor designates the vascular channels that are different in the time taken until the contrast agent flows in, the regions dominated by the respective vascular channels can be imaged by different hues, and thus the dominant region can be easily discriminated. As a result, for example, a precise examination can be performed on arterializations of the blood vessels of the liver reported as the blood flow moving state in the liver of the patient who has a diffuse liver disease. For example, the regions respectively dominated by the portal vein and the artery are discriminated through the ultrasonic diagnosis apparatus 10 according to the present embodiment, and thus the degree of arterializations of the blood vessels of the liver can be intuitively recognized.

Further, according to the first embodiment, the detecting unit 143a uses the brightness of pixels of the angiogram included in the region of interest as the intensity of the reflective wave signal. Thus, the ultrasonic diagnosis apparatus 10 according to the first embodiment can decide the reaching time of the contrast agent by a simple method without using raw data.

Further, according to the first embodiment, the deciding unit 143b determines a time, at which the ratio of the number of pixels whose brightness has reached the predetermined brightness among pixels configuring the region of interest has exceeded the predetermined threshold value, as the reaching time. Alternatively, the deciding unit 143b determines a time, at which average brightness that is an average of brightness of pixels configuring the region of interest has exceeded the predetermined threshold value, as the reaching time. Thus, the ultrasonic diagnosis apparatus 10 according to the first embodiment can variously set the reaching time of the contrast agent and flexibly execute an examination.

Further, according to the first embodiment, the generating unit 143c generates a frequency distribution in which the reaching time of each of the pixels included in the angiogram or the region of interest or the hue on the hue conversion image is associated with the number of pixels. The control unit 160 displays the frequency distribution generated by the generating unit 143c on the monitor 13. Thus, the ultrasonic diagnosis apparatus 10 according to the first embodiment can help the doctor make a more accurate determination on the ultrasonic examination.

Further, according to the first embodiment, the generating unit 143c generates the hue conversion image after correcting the deviation between the angiograms used for generating the hue conversion image. Thus, the ultrasonic diagnosis apparatus 10 according to the first embodiment can generate a hue conversion image that is not influenced, for example, by the shaking of a moving body or the ultrasonic probe and that is accurately consistent with the examination target portion.

(Second Embodiment)

The first embodiment has been described in connection with the case in which the region of interest is designated for each vascular channel. A second embodiment will be described in connection with a case in which a plurality of vascular channels are designated as one region of interest. A description will be made below in connection with a case in which two vascular channels are designated as one region of interest, but the present embodiment is not limited thereto. The number of vascular channels included in the region of interest may be arbitrary. For example, three vascular channels may be included in the region of interest.

Figure 10:
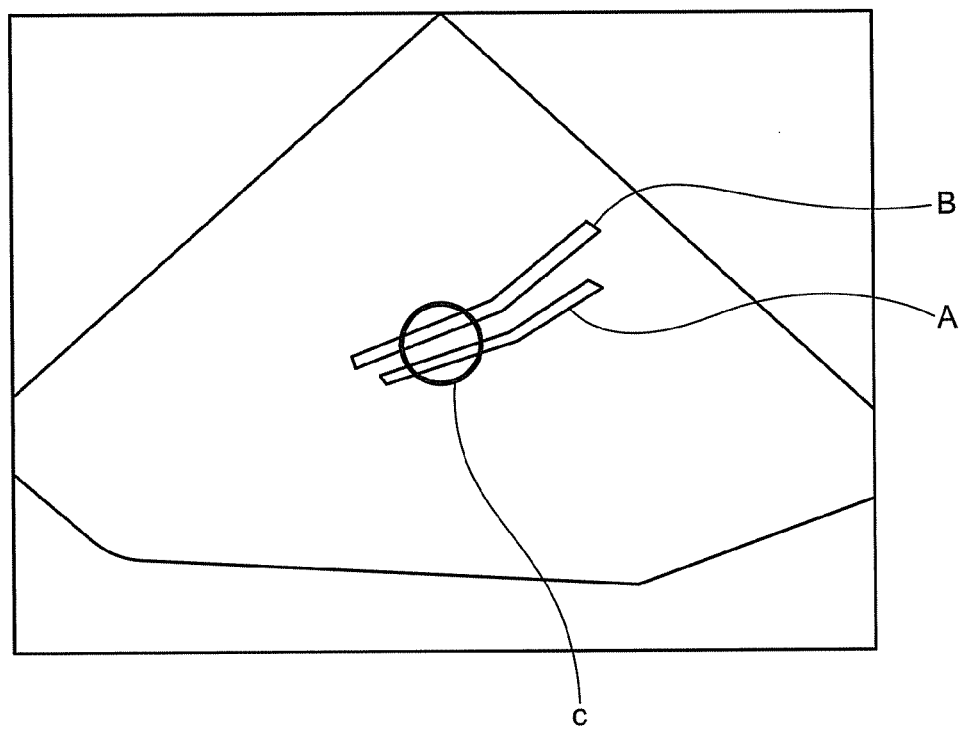
FIG. 10 is a diagram for explaining a region of interest according to a second embodiment.

FIG. 10 is a diagram for explaining a region of interest according to the second embodiment. FIG. 10 illustrates an angiogram of the liver of the subject P dosed with the contrast agent, and the liver parenchyma and vascular channels are shown. For example, it is assumed that the operator of the ultrasonic diagnosis apparatus 10, the doctor, or the like has designated a region c of interest including the vascular channel A and the vascular channel B as illustrated in FIG. 10. For example, the vascular channel A is the hepatic artery. Further, for example, the vascular channel B is the portal vein. A frame of any one of a plurality of angiograms obtained at the time of ultrasonic examination of the subject P may be used as an image in which the region of interest is designated.

The deciding unit 143b decides each of reaching times at which the intensity of the reflective wave signal detected by the detecting unit 143a has reached a plurality of threshold values. Specifically, the deciding unit 143b decides the times at which the average brightness that is an average of brightness of all pixels in the region of interest have reached the threshold values that are set in a stepwise fashion, respectively.

Figure 11:
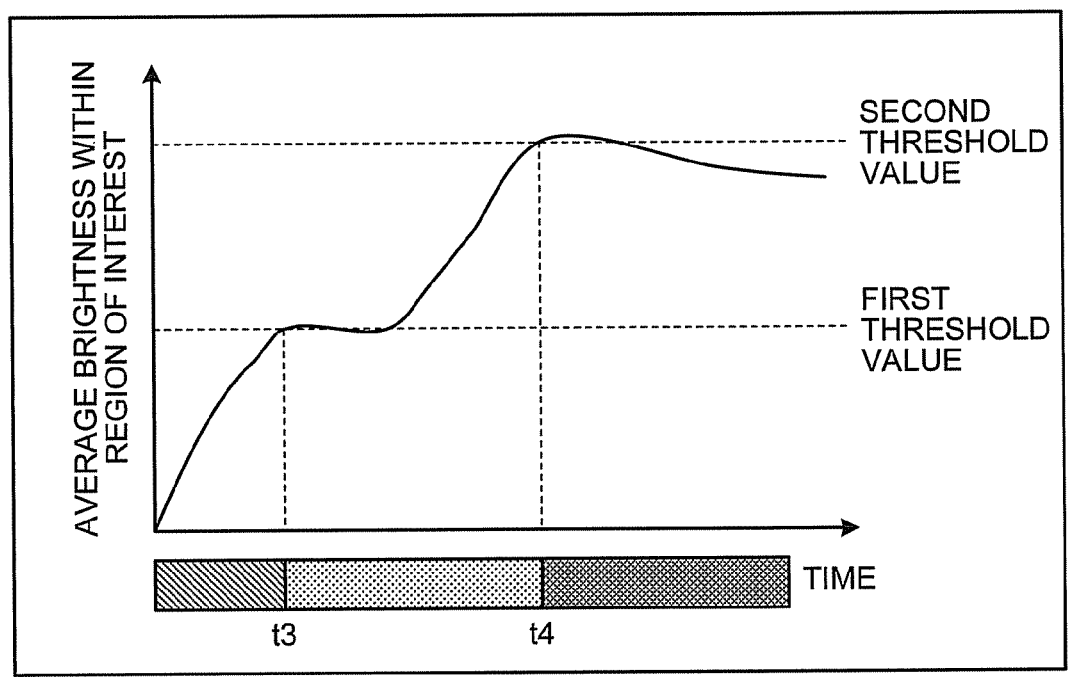
FIG. 11 is a diagram illustrating an example of deciding a contrast agent reaching time when one region of interest includes a plurality of vascular channels.

FIG. 11 is a diagram for explaining an example of determining the contrast agent reaching time when a plurality of vascular channels are included in one region of interest. In FIG. 11, the horizontal axis represents time, and the vertical axis represents average brightness within the region of interest. FIG. 11 illustrates an example of determining whether or not the contrast agent has reached the region c of interest illustrated in FIG. 10. For example, the deciding unit 143b decides a time t3 at which the average brightness of the region c of interest has reached a first threshold value as illustrated in FIG. 11. Then, the deciding unit 143b decides a time t4 at which the average brightness of the region c of interest has reached a second threshold value.

The generating unit 143c changes the hue at the new reaching time decided by the deciding unit 143b and so generates the hue conversion image in which regions having reached a predetermined threshold value at different reaching times are represented by different hues. For example, the generating unit 143c generates the hue conversion image and the hue conversion table in which the hue changes at the time t3 and the time t4 decided by the deciding unit 143b.

Figure 12:
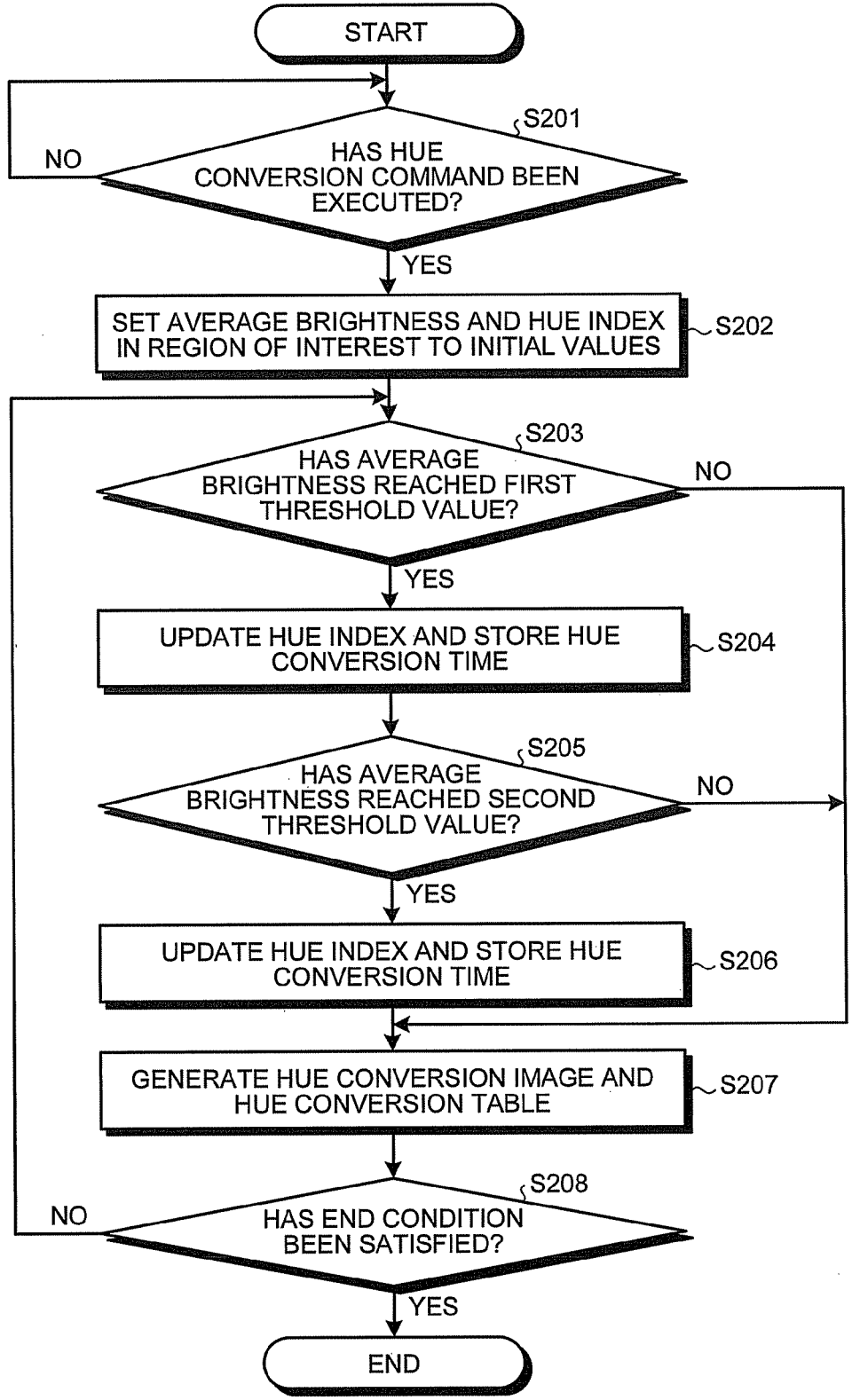
FIG. 12 is a flowchart illustrating a procedure of a process performed by an ultrasonic diagnosis apparatus according to the second embodiment.

Next, a process performed by the ultrasonic diagnosis apparatus 10 according to the second embodiment will be described with reference to FIG. 12. FIG. 12 is a flowchart illustrating a procedure of the process performed by the ultrasonic diagnosis apparatus 10 according to the second embodiment. In particular, FIG. 12 illustrates a process after the operator, the doctor, or the like has designated the region of interest in an angiogram of the subject P. As illustrated in FIG. 12, in the ultrasonic diagnosis apparatus 10 according to the second embodiment, when a hue conversion command is executed (Yes in step S201), the deciding unit 143b sets the average brightness of the region of interest and a hue index to initial values (step S202).

Then, the detecting unit 143a detects the brightness of each of pixels included in the region of interest, and the deciding unit 143b determines, within the region of interest where the contrast agent has not reached, whether or not the average brightness of the region of interest has reached the first threshold value (step S203). Here, when the average brightness has reached the first threshold value (Yes in step S203), the deciding unit 143b updates the hue index and stores a hue conversion time in the image memory 150 (step S204).

Thereafter, the deciding unit 143b determines whether or not the average brightness of the region of interest has reached the second threshold value in the region of interest whose average brightness has reached the first threshold value (step S205). Here, when the average brightness has reached the second threshold value (Yes in step S205), the deciding unit 143b updates the hue index and stores a hue conversion time in the image memory 150 (step S206). Then, the generating unit 143c generates the hue conversion image and the hue conversion table with reference to the hue indices and the hue conversion times for the first threshold value and the second threshold value stored in the image memory 150 (step S207).

Meanwhile, when it is determined in step S203 that the average brightness has not reached the first threshold value (No in step S203), the generating unit 143c generates the hue conversion image and the hue conversion table with reference to the non-updated hue index stored in the image memory 150 (step S207). Further, when it is determined in step S205 that the average brightness has not reached the second threshold value (No in step S205), the generating unit 143c generates the hue conversion image and the hue conversion table with reference to the non-updated hue index stored in the image memory 150 and the hue index and the hue conversion time for the first threshold value (step S207).

Then, the generating unit 143c determines whether or not the end condition has been satisfied (step S208). When the end condition has not been satisfied (No in step S208), the process returns to step S203, and the deciding unit 143b determines, within the region of interest which the contrast agent has not reached, whether or not the average brightness has reached the first threshold value. However, when the end condition has been satisfied (Yes in step S208), the ultrasonic diagnosis apparatus 10 finishes the process. The end condition in step S208 may be satisfied when all the frames designated by the operator, the doctor, or the like have been processed.

As described above, according to the second embodiment, the deciding unit 143b decides each of the reaching times at which the intensity of the reflective wave signal detected by the detecting unit 143a has reached a plurality of different threshold values. Then, the generating unit 143c changes the hue at the new reaching time decided by the deciding unit 143b and generates the hue conversion image in which regions having reached the predetermined threshold value at the different reaching times are represented by different hues. Thus, the ultrasonic diagnosis apparatus 10 according to the second embodiment can image dominant regions of different vascular channels with different hues even when it is difficult to designate two regions of interest in a region where vascular regions are concentrated or the like, so that dominant regions of different vascular channels can be easily discriminated.

(Third Embodiment)

The first embodiment and the second embodiment have been described above, but various forms of embodiments, which is different from the first embodiment and the second embodiment, can be embodied.

In the above embodiments, the image generating unit 140 functions as an image generating unit that generates a medical image (an ultrasonic image). The deciding unit 143b functions as a time detecting unit that detects reaching times at which the contrast agent has reached a predetermined region of the medical image (the ultrasonic image). The deciding unit 143b functions as a color map setting unit that sets a color map in which the reaching times are associated with hues based on the first inflow time corresponding to the first designation region set by the medical image (the ultrasonic image) and a second inflow time corresponding to a second designation region. The generating unit 143c functions as a generating unit that generates the hue conversion image in which the hue is allocated to each region of the medical image based on the color map and the reaching time in each region of the medical image (the ultrasonic image). The control unit 160 functions as a display control unit that displays the hue conversion image on the monitor 13. However, these functional blocks may be arbitrarily modified.

(1) Setting of Region of Interest

The first embodiment and the second embodiment have been described in connection with the case in which the hue conversion image and the hue conversion table are generated based on the initially designated region of interest. However, the present embodiment is not limited thereto. For example, after the hue conversion image and the hue conversion table are generated, the initially designated region of interest may be moved, and the hue conversion image and the hue conversion table may be generated based on the moved region of interest.

Figure 13:
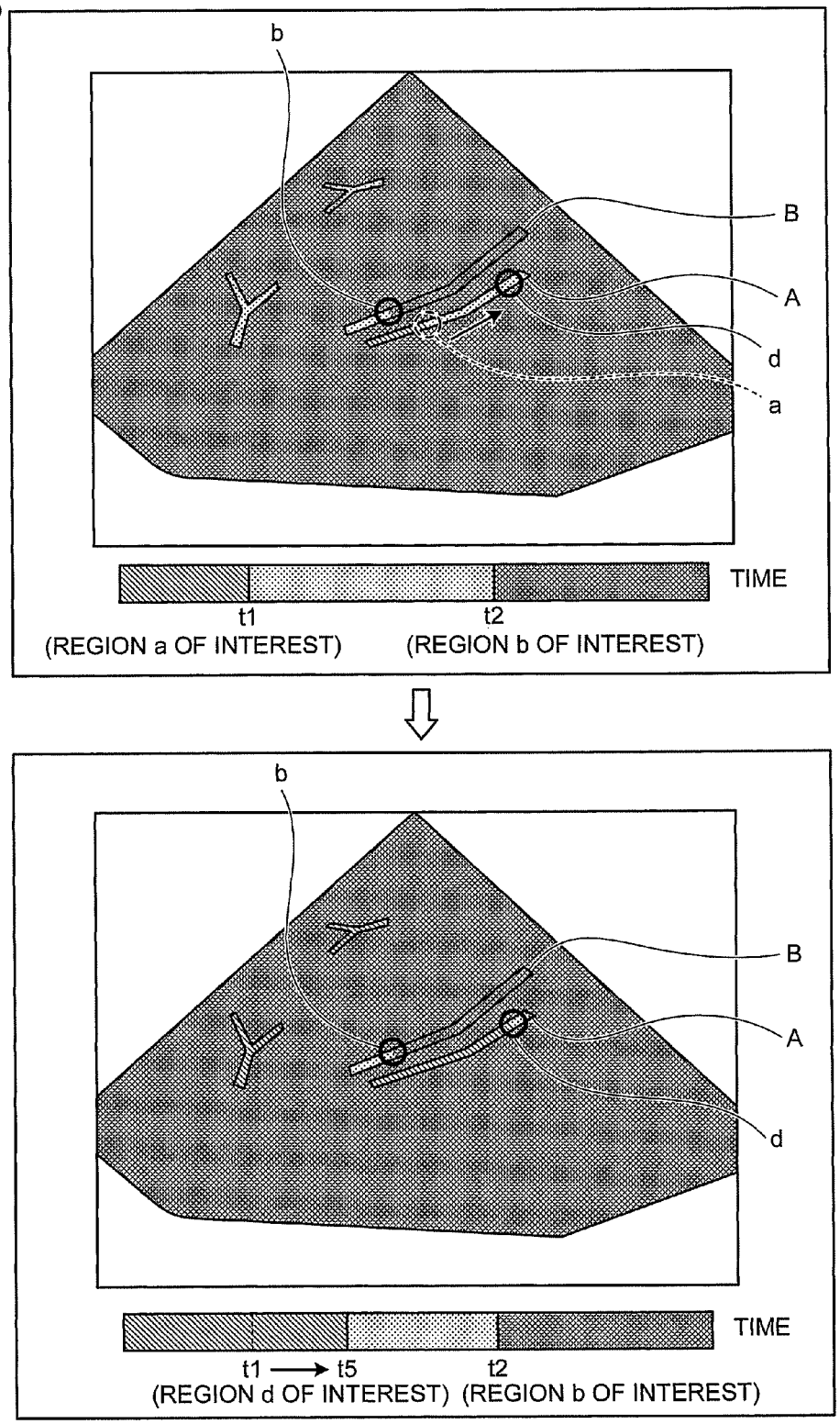
FIG. 13 is a diagram for explaining an example of setting a region of interest after generation of a hue conversion image and a hue conversion table.

For example, the deciding unit 143b decides the reaching time on the moved region of interest again when the position of the region of interest on the ultrasonic image changes. Then, the generating unit 143c converts the hue conversion image into an image in which the hue is changed at the reaching time decided again by the deciding unit 143b. FIG. 13 is a diagram for explaining an example of setting the region of interest after generating the hue conversion image and the hue conversion table. FIG. 13 illustrates a case in which the region a of interest and the region b of interest are set, the hue conversion image and the hue conversion table are generated, and then the region a of interest moves.

When the operator, the doctor, or the like has moved the region a of interest to the position of a region d of interest as illustrated in an upper drawing of FIG. 13, the deciding unit 143b decides a reaching time t5 of the contrast agent on the region d of interest as illustrated in a lower drawing of FIG. 13. For example, the detecting unit 143a detects the brightness of pixels included in the region d of interest. Then, the deciding unit 143b decides the reaching time t5 of the contrast agent on the region d of interest based on the brightness of pixels of the region d of interest detected by the detecting unit 143a.

Then, the generating unit 143c generates the hue conversion image and the hue conversion table when the region of interest has moved as illustrated in a lower drawing FIG. 13. Thus, the operator, the doctor, or the like can see the hue conversion image whose hue has arbitrarily changed while confirming the shape of the blood vessels through the image and clearly recognizing the separation of the artery or the vein, an inflow process of the blood flow inside a tumor, or the like. Further, any one of the histological images, the angiogram, and the hue conversion image may be used as an image used for re-setting the region of interest.

(2) Change of Hue

The first embodiment and the second embodiment have been described in connection with the case in which the hue conversion image is generated using a previously set hue. However, the present embodiment is not limited thereto. For example, the hue may be changed according to an interval of the reaching time of the contrast agent.

For example, the generating unit 143c changes the hue to use according to the interval of the time decided by the deciding unit 143b with respect to a single region of interest or each of a plurality of regions of interest. In this case, information in which the time interval is associated with the hue is stored in the image memory 150 or the internal storage unit 170, and the generating unit 143c changes the hue with reference to the information. An example of changing the hue will be described below with reference to FIGS. 14A and 14B. FIG. 14A is a diagram illustrating a hue conversion table generated by an ultrasonic examination of a subject P1. FIG. 14B is a diagram illustrating a hue conversion table generated by an ultrasonic examination of a subject P2.

For example, the interval between the reaching time t1 and the reaching time t2 illustrated in the upper drawing of FIG. 14B is shorter than the interval illustrated in FIG. 14A, and thus the generating unit 143c generates a hue conversion table in which the hue 3 is changed to a hue 4 as illustrated in a lower drawing of FIG. 14B. Thus, the operator, the doctor, or the like can more clearly recognize, for example, a disease whose feature is in the interval of the reaching time.

(3) Change of Hue

The first embodiment and the second embodiment have been described in connection with the case in which the hue conversion image is generated using a previously set hue. However, the present embodiment is not limited thereto. For example, the hue may be changed after generation of the hue conversion image and the hue conversion table.

In this case, for example, when the hue of the hue conversion table is changed, the generating unit 143c changes the hue of the generated hue conversion image based on the changed hue conversion table. Thus, the operator, the doctor, or the like can clearly recognize a disease or the like since regions difficult to discriminate can be made clear.

(4) Processing Target

The first embodiment and the second embodiment have been described in connection with the case of using a two-dimensional ultrasonic image (angiogram). However, the present embodiment is not limited thereto. For example, a three-dimensional ultrasonic image (angiogram) may be used. In this case, the hue conversion image is displayed as a rendering image from a certain designation direction or displayed by a multi planar reformation (MPR) image cut by a predetermined cross section.

(5) Gradation Display of Hue

The first embodiment and the second embodiment have been described in connection with the case of using the hue conversion image (color map) and the hue conversion table of a single color. However, an embodiment is not limited thereto. For example, the hue of the same time interval may be displayed by a gradation of the same type of color.

Figure 15:
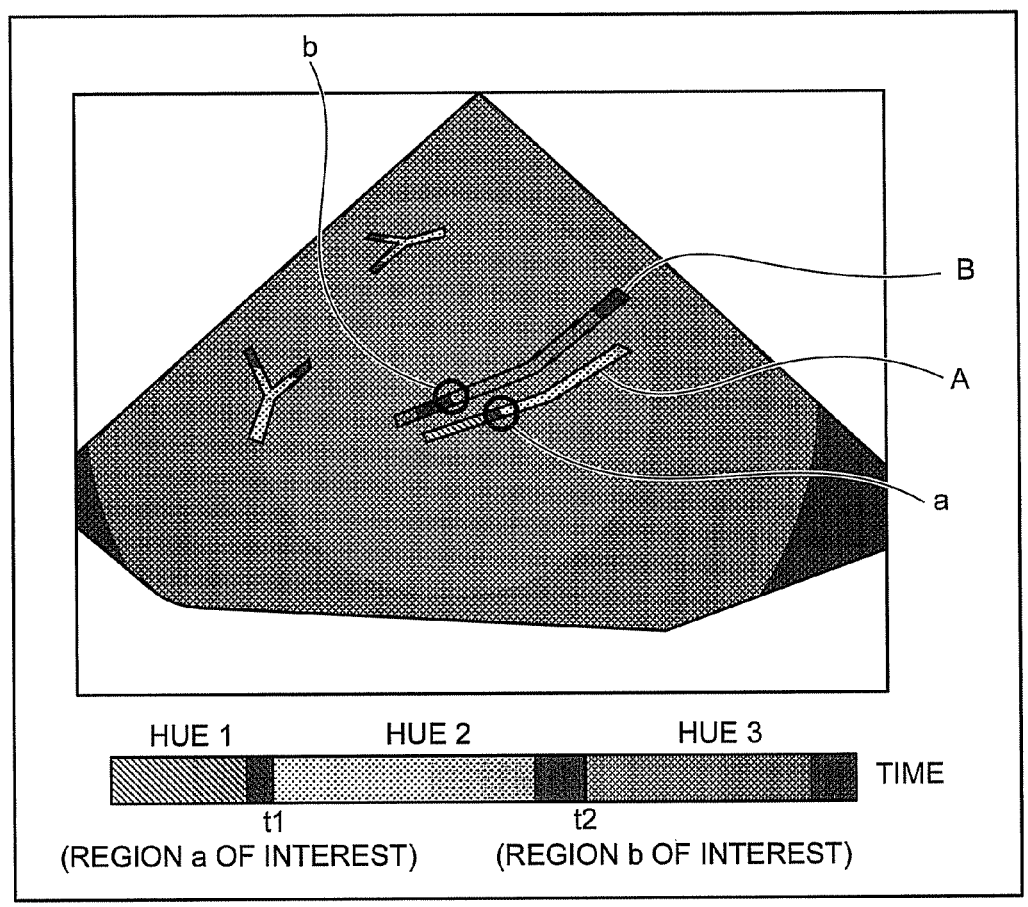
FIG. 15 is a diagram for explaining an example of gradation display of a hue conversion image and a hue conversion table.

FIG. 15 is a diagram for explaining an example of gradation display of the hue conversion image and the hue conversion table. FIG. 15 illustrates the hue conversion image and the hue conversion table of the angiogram illustrated in FIG. 3. For example, the generating unit 143c generates the hue conversion image and the hue conversion table in which gradation by the same type of color is applied to each of the hue 1, the hue 2, and the hue 3 within the elapsed time as illustrated in FIG. 15. For example, the generating unit 143c generates the hue conversion image in which the flow of the contrast agent from the left end of the vascular channel A to the region a of interest is represented by the hue 1 that changes by the same type of color from a light color to a dark color, the flow of the contrast agent until the contrast agent reaches the region b of interest after the contrast agent reaches the region a of interest is represented by the hue 2 that changes by the same type of color different from the hue 1 from a light color to a dark color, and the flow of the contrast agent after the contrast agent reaches the region b of interest is represented by the hue 3 that changes by the same type of color different from the hue 1 and the hue 3 from a light color to a dark color as illustrated in FIG. 15.

Further, the generating unit 143c generates the hue conversion table in which the time until the reaching time t1 after the contrast agent is dosed is represented by the hue 1, the time between the reaching time t1 and the reaching time t2 is represented by the hue 2, and the time after the reaching time t2 is represented by the hue 3 as illustrated in FIG. 15.

As described above, since the flow of the contrast agent is displayed by gradation, it is possible to easily observe the flow of blood inside the vascular channel or how blood has been sent to the liver parenchyma as illustrated in FIG. 15. As the hue conversion image displayed by gradation illustrated in FIG. 15, the hue conversion image is generated for each of all frames similarly to the above embodiments, and one hue conversion image color-mapped using all of them is illustrated. However, the hue conversion images of all frames may be displayed in time series order as a moving image.

(Fourth Embodiment)

The first embodiment, the second embodiment, and the third embodiment have been described in connection with the case in which the ultrasonic diagnosis apparatus is used as the medical image diagnosis apparatus (modality). However, an embodiment is not limited thereto. For example, another modality such as an X-ray computed tomography (CT) apparatus or an X-ray diagnosis apparatus may be used. A description will be made below in connection with a case of using the X-ray CT apparatus.

Figure 16:
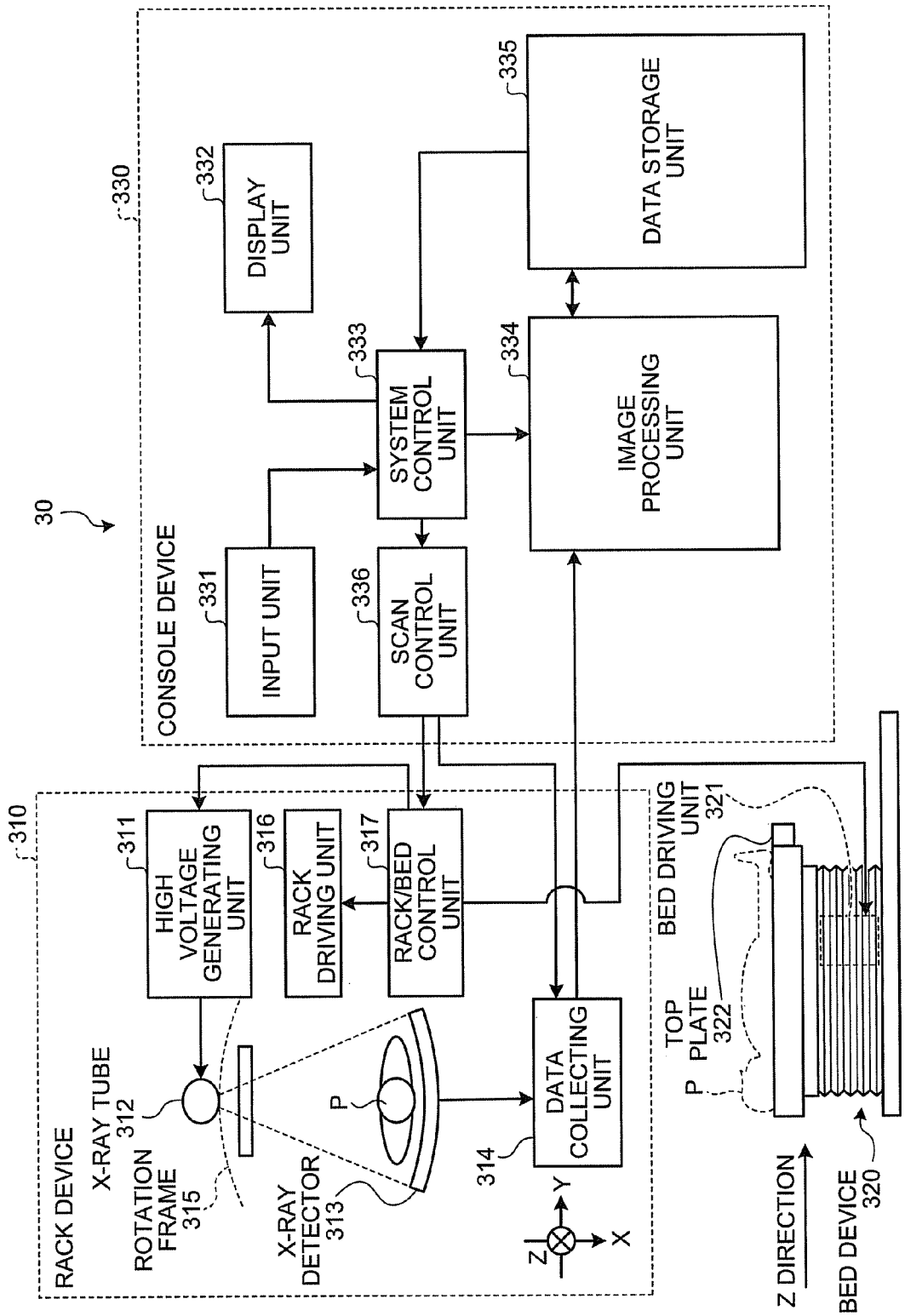
FIG. 16 is a diagram for explaining a configuration of an X-ray CT apparatus according to a fourth embodiment.

A configuration of the X-ray CT apparatus according to a fourth embodiment will be described with reference to FIG. 16. FIG. 16 is a diagram illustrating a configuration example of an X-ray CT apparatus 30 according to the fourth embodiment. The X-ray CT apparatus 30 according to the fourth embodiment includes a rack device 310, a bed device 320, and a console device 330 as illustrated in FIG. 16.

The rack device 310 irradiates the subject P with an X-ray, detects an X-ray having passed through the subject P, and outputs the detected X-ray to the console device 330. The rack device 310 includes a high voltage generating unit 311, an X-ray tube 312, an X-ray detector 313, a data collecting unit 314, a rotation frame 315, a rack driving unit 316, and a rack/bed control unit 317.

The high voltage generating unit 311 supplies the X-ray tube 312 with a high voltage according to the controls by the rack/bed control unit 317. The X-ray tube 312 is a vacuum tube that generates an X-ray by a high voltage supplied from the high voltage generating unit 311 and irradiates the subject P with the X-ray with the rotation of the rotation frame 315. That is, the high voltage generating unit 311 adjusts the amount of the X-ray irradiated to the subject P by adjusting the tube voltage or the tube current supplied to the X-ray tube 312.

The X-ray detector 313 is a two-dimensional array-type detector (a plane detector) that detects the X-ray having passed through the subject P. The X-ray detector 313 includes a plurality of detecting element rows which each includes X-ray detecting elements arranged corresponding to a plurality of channels and that are arranged along the body axis of the subject P (a Z axis direction illustrated in FIG. 16). Specifically, the X-ray detector 313 according to the fourth embodiment includes X-ray detecting elements arranged in multiple rows, for example, 320 rows, along the body axis of the subject P and can detect the X-ray having passed through the subject P widely, for example, in a range including the lung or the heart of the subject P.

The data collecting unit 314 generates the projection data using the X-ray detected by the X-ray detector 313 and transmits the generated projection data to an image processing unit 334 of the console device 330. The rotation frame 315 is an annular frame that rotates on the subject P at a high speed and continuously, and the X-ray tube 312 is arranged to face the X-ray detector 313.

The rack driving unit 316 drives a rack according to the controls by the rack/bed control unit 317. Specifically, the rack driving unit 316 continuously rotates the rotation frame 315 at a high speed by driving a motor and continuously rotates the X-ray tube 312 and the X-ray detector 313 on the subject P along a circular orbit. The rack/bed control unit 317 controls the high voltage generating unit 311, the rack driving unit 316, and a bed driving unit 321 according to the controls by a scan control unit 336 which will be described later.

The bed device 320 is a pedestal on which the subject P of a shooting target is placed and includes the bed driving unit 321 and a top plate 322. The bed driving unit 321 continuously reciprocates the top plate 322 along the body axis of the subject P by driving a motor according to control by the rack/bed control unit 317. The top plate 322 is a plate on which the subject P is placed.

In the examination by the X-ray CT apparatus 30, a scanogram obtained by scanning the whole body of the subject P along the body axis direction is captured by moving the top plate 322 while irradiating the X-ray from the X-ray tube 312 in a state in which the rotation frame 315 is fixed. Then, the operator, who has referred to the scanogram of the subject P, makes a shooting plan of an X-ray CT image. For example, the rack device 310 executes a helical scan of helically scanning the subject P by rotating the rotation frame 315 while moving the top plate 322. Alternatively, the rack device 310 executes a conventional scan of scanning the subject P along the circular orbit by moving the top plate 322 and then rotating the rotation frame 315 in a state in which the position of the subject P is fixed.

The console device 330 includes an input unit 331, a display unit 332, a system control unit 333, an image processing unit 334, a data storage unit 335, and a scan control unit 336 as illustrated in FIG. 16. The console device 330 receives an operation of the X-ray CT apparatus 30 by the operator and reconfigures an X-ray CT image based on the projection data collected by the rack device 310.

The input unit 331 includes a mouse, a keyboard, or the like which is used for the operator of the X-ray CT apparatus 30 to input various instructions or various setting and transmits the information of an instruction or setting received from the operator to the system control unit 333. For example, the input unit 331 receives an operation related to the setting of a scan plan and a reconfiguration plan, an edit operation related to the various settings for displaying the medical image on a three-dimensional monitor, or the like from the operator. Further, the X-ray CT apparatus 30 can help the operator select an optimum scan plan from among the scan plans to which various conditions are set in advance according to the attribute information (the sex, the age, or the physique) of the subject P, an examination purpose, an examination portion, or the like at the time of setting of the scan plan. The previously set scan plan is called an "expert plan (EP)".

The display unit 332 is a display such as a liquid crystal display (LCD) and displays various pieces of information. For example, the display unit 332 displays an X-ray image stored in the data storage unit 335, a graphical user interface (GUI) for receiving various instructions from the operator, or the like.

The system control unit 333 controls the whole X-ray CT apparatus 30 by controlling the rack device 310, the bed device 320, and the console device 330. For example, the system control unit 333 controls the scan control unit 336 such that three-dimensional projection data is collected. Further, for example, the system control unit 333 controls the image processing unit 334 such that the X-ray CT image is reconfigured based on the three-dimensional projection data.

Then, the system control unit 333 performs the controls such that the display unit 332 displays the X-ray CT image generated by the image processing unit 334, the hue conversion image, the hue conversion data, or the like.

In the fourth embodiment, the system control unit 333 executes a dynamic scan as a main scan. Here, the dynamic scan refers to a technique of reconfiguring a dynamic state image of a portion (for example, the liver) that becomes the shooting target by repetitively irradiating a range including the portion that becomes the shooting target with the X-ray. Through the dynamic scan, it is possible to observe how the contrast agent flows to the shooting target portion.

The dynamic scan may be performed by simultaneously detecting the X-rays having passed through the range including the shooting target portion using multiple rows of plane detectors as the X-ray detector 313. However, for example, the dynamic scan may be performed by reciprocating the top plate 322 in a slice direction and repetitively irradiating the range including the shooting target portion with the X-ray in a helical form.

The image processing unit 334 performs various processes on the three-dimensional projection data received from the data collecting unit 314. Specifically, the image processing unit 334 reconfigures a three-dimensional X-ray CT image (which is also described below as "volume data") by performing pre-processing such as sensitivity correction on the three-dimensional projection data received from the data collecting unit 314 and performing a back projection process on the pre-processed three-dimensional projection data. Then, the image processing unit 334 stores the reconfigured volume data in the data storage unit 335. Further, the image processing unit 334 generates a stereoscopic X-ray CT image, for example, by using a shaded volume rendering (SVR) technique or generating a cross-sectional image of an arbitrary surface and storing the generated X-ray CT image in the data storage unit 335.

The data storage unit 335 stores the volume data or the X-ray CT image reconfigured by the image processing unit 334 or the like. The scan control unit 336 controls the rack/bed control unit 317 and the data collecting unit 314 based on the scan condition instructed from the system control unit 333.

The whole configuration of the X-ray CT apparatus 30 according to the fourth embodiment has been described above. Under this configuration, the X-ray CT apparatus 30 according to the fourth embodiment is configured to image dominant regions of different vascular channels by a simple operation through a process of the image processing unit 334 which will be described below in detail so that dominant regions of different vascular channels can be easily discriminated. Specifically, on the subject P dosed with the contrast agent, the image processing unit 334 according to the fourth embodiment images the dominant region of the vascular channel into which the contrast agent flows fast and the dominant region of the vascular channel into which the contrast agent flows slowly with different hues. As a result, the dominant regions of the different vascular channels can be easily discriminated through the X-ray CT apparatus 30 according to the fourth embodiment.

Figure 17:
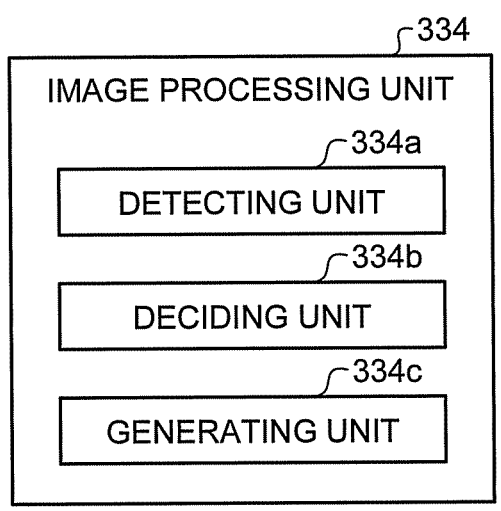
FIG. 17 is a diagram for explaining a configuration of an image processing unit according to the fourth embodiment.

A process of the image processing unit 334 according to the fourth embodiment will be described in detail with reference to FIG. 17. FIG. 17 is a diagram for explaining a configuration of the image processing unit according to the fourth embodiment. The image processing unit 334 includes a detecting unit 334a, a deciding unit 334b, and a generating unit 334c as illustrated in FIG. 17. The detecting unit 334a detects an index value representing a contrast agent density within the region of interest set to an image that is reconfigured during shooting. Specifically, the detecting unit 334a reads the reconfigured X-ray CT image out of the data storage unit 335 each time when the X-ray CT image is reconfigured by the image processing unit 334.

Then, each time when the X-ray CT image is read out, the detecting unit 334a detects the CT value on the region of interest set to each X-ray CT image and stores the detected CT value in an internal memory (not shown) or the like in time series. Here, the region of interest that is a region in which the CT value is detected is set via the input unit 331 by the operator. Further, the detecting unit 334a notifies the deciding unit 334b of the detected CT value. The fourth embodiment has been described in connection with the technique of using the CT value as the index value representing the contrast agent density as described above. However, any other value may be used other than the CT value, as long as the value can represent the contrast agent density.

The deciding unit 334b detects the reaching time at which the contrast agent has reached the predetermined region of the medical image. Specifically, in the CT value of the X-ray CT image detected by the detecting unit 334a, the deciding unit 334b may determine the time, at which the ratio of the number of pixels whose CT value has reached a predetermined CT value among pixels configuring the region of interest has exceeded the predetermined threshold value, as the reaching time. Alternatively, the deciding unit 334b may determine the time at which an average CT value that is an average of the CT values of pixels configuring the region of interest has exceeded the predetermined threshold value as the reaching time.

Further, the deciding unit 334b sets a color map in which the reaching times are associated with hues based on the first inflow time corresponding to the first designation region set to the X-ray CT image and the second inflow time corresponding to the second designation region. Specifically, the deciding unit 334b sets a color map in which the reaching time between the first inflow time and the second inflow time is associated with the first hue, and the reaching time after the second inflow time is associated with the second hue.

The generating unit 334c generates the hue conversion image in which the hue is allocated to each region of the X-ray CT image based on the color map set by the deciding unit 334b and the reaching time in each region of the X-ray CT image. Specifically, in a plurality of X-ray CT images of the subject P, the generating unit 334c generates the hue conversion image in which the region whose CT value by the contrast agent is detected as having increased between the reaching time of the contrast agent in one region of interest and the reaching time of the contrast agent in another region of interest is represented by the same hue. Further, the generating unit 334c generates the hue conversion table in which the hues allocated in the hue conversion image are represented along the time axis. The generating unit 334c stores the generated hue conversion image and the hue conversion table in the data storage unit 335.

Here, the generating unit 334c generates the hue conversion image after correcting the deviations between the X-ray CT images used for generating the hue conversion image. Specifically, the generating unit 334c generates the hue conversion image in which the positional deviations between the X-ray CT images of different time phases caused by the subject P's breathing or the like has been corrected. For example, the generating unit 334c executes a non-linear warping process or a linear positioning process such as parallel displacement or rotation.

Further, the generating unit 334c generates a frequency distribution in which the time at which the CT value in each of pixels included in the X-ray CT image or the region of interest has reached a predetermined threshold value or a hue on the hue conversion image is associated with the number of pixels and stores the frequency distribution in the data storage unit 335.

The process by the X-ray CT apparatus 30 according to the fourth embodiment is different from the process by the ultrasonic diagnosis apparatus 10 according to the first embodiment in that the CT value included in the medical image data is used. A procedure of the process by the X-ray CT apparatus 30 according to the fourth embodiment will be described with reference to FIG. 9.

That is, in the X-ray CT apparatus 30 according to the fourth embodiment, as illustrated in FIG. 9, when a hue conversion command is executed (Yes in step S101), the deciding unit 334b sets a flag representing the contrast agent reaching state in each region of interest, the ratio of pixels which the contrast agent has reached, and a hue index as initial values (step S102).

Then, the detecting unit 334a detects the CT value of each of the pixels included in each region of interest, and the deciding unit 334b determines, within the region of interest which the contrast agent has not reached, whether or not the ratio of pixels, which indicates the contrast agent having reached, has reached a predetermined threshold value (step S103). Here, when the ratio of pixels which the contrast agent has reached has reached the predetermined threshold value (Yes in step S103), the deciding unit 334b updates the reaching flag and the hue index and stores the hue conversion time in the data storage unit 335 (step S104). Then, the generating unit 334c generates the hue conversion image and the hue conversion table with reference to the hue index and the hue conversion time stored in the data storage unit 335 (step S105).

Meanwhile, when it is determined in step S103 that the ratio of pixels which the contrast agent has reached has not reached the predetermined threshold value (No in step S103), the generating unit 334c generates the hue conversion image and the hue conversion table (step S105). That is, the generating unit 334c generates the hue conversion image and the hue conversion table with reference to the non-updated hue index stored in the data storage unit 335.

Then, the generating unit 334c determines whether or not the end condition has been satisfied (step S106). Here, when the end condition has not been satisfied (No in step S106), the process returns to step S103, and the deciding unit 334b determines, within the region of interest which the contrast agent has not reached, whether or not the ratio of pixels indicating the contrast agent having reached becomes a predetermined threshold value. However, when the end condition has been satisfied (Yes in step S106), the X-ray CT apparatus 30 finishes the process. The end condition in step S106 may be satisfied when all the frames designated by the operator, the doctor, or the like have been processed.

The X-ray CT apparatus 30 according to the fourth embodiment can designate a plurality of regions of interest as one region of interest similarly to the ultrasonic diagnosis apparatus according to the second embodiment. This case will be described below.

The deciding unit 334b decides each of the reaching times at which the CT value detected by the detecting unit 334a has reached a plurality of different threshold values. Specifically, the deciding unit 334b decides the times at which the average CT value that is an average of CT values of all pixel in the region of interest has reached threshold values that are set in a stepwise fashion, respectively.

The generating unit 334c changes the hue at the new reaching time decided by the deciding unit 334b and so generates the hue conversion image in which regions having reached at a predetermined threshold value at different reaching times are represented by different hues and the hue conversion table.

The process by the X-ray CT apparatus 30 according to the fourth embodiment is different from the process by the ultrasonic diagnosis apparatus 10 according to the second embodiment in that the average CT value is used to decide the reaching time of the contrast agent. A procedure of the process by the X-ray CT apparatus 30 according to the fourth embodiment will be described with reference to FIG. 12.

In the X-ray CT apparatus 30 according to the fourth embodiment, as illustrated in FIG. 12, when a hue conversion command is executed (Yes in step S201), the deciding unit 334b sets the average CT value of the region of interest and a hue index to the initial values (step S202).

Then, the detecting unit 334a detects the average CT value of each pixel included in the region of interest, and the deciding unit 334b determines, within the region of interest which the contrast agent has not reached, whether or not the average CT value of the region of interest has reached the first threshold value (step S203). Here, when the average CT value has reached the first threshold value (Yes in step S203), the deciding unit 334b updates the hue index and stores the hue conversion time in the data storage unit 335 (step S204).

Thereafter, the deciding unit 334b determines whether or not the average CT value of the region of interest has reached the second threshold value in the region of interest whose average CT value has reached the first threshold value (step S205). Here, when the average CT value has reached the second threshold value (Yes in step S205), the deciding unit 334b updates the hue index and stores a hue conversion time in the data storage unit 335 (step S206). Then, the generating unit 334c generates the hue conversion image and the hue conversion table with reference to the hue indices and the hue conversion times for the first threshold value and the second threshold value stored in the data storage unit 335 (step S207).

Meanwhile, when it is determined in step S203 that the average CT value has not reached the first threshold value (No in step S203), the generating unit 334c generates the hue conversion image and the hue conversion table with reference to the non-updated hue index stored in the data storage unit 335 (step S207). Further, when it is determined in step S205 that the average CT value has not reached the second threshold value (No in step S205), the generating unit 334c generates the hue conversion image and the hue conversion table with reference to the non-updated hue index stored in the data storage unit 335 and the hue index and the hue conversion time for the first threshold value (step S207).

Then, the generating unit 334c determines whether or not the end condition has been satisfied (step S208). When the end condition has not been satisfied (No in step S208), the process returns to step S203, and the deciding unit 334b determines within the region of interest which the contrast agent has not reached whether or not the average CT value has reached the first threshold value. However, when the end condition has been satisfied (Yes in step S208), the X-ray CT apparatus 30 finishes the process. The end condition in step S208 may be satisfied when all frames designated by the operator, the doctor, or the like have been processed.

The X-ray CT apparatus 30 according to the fourth embodiment may move the initially designated region of interest after generating the hue conversion image and the hue conversion table and generate the hue conversion image and the hue conversion table based on the moved region of interest. In this case, when the position of the region of interest on the X-ray CT image is moved, the deciding unit 334b decides the reaching time in the moved region of interest again. Then, the generating unit 334c converts the hue conversion image into an image in which the hue is changed at the reaching time decided again by the deciding unit 334b. Thus, the operator, the doctor, or the like can see the hue conversion image whose hue has arbitrarily changed while confirming the shape of the blood vessels on the image and clearly recognizing the separation of the artery or the vein, an inflow process of the blood flow inside a tumor, or the like. Further, any one of the histological images, the angiogram, and the hue conversion image may be used as an image used for re-setting the region of interest.

The X-ray CT apparatus 30 according to the fourth embodiment may change the hue according to an interval of the reaching time of the contrast agent. In this case, the generating unit 334c changes the hue to use according to the interval of the time decided by the deciding unit 334b with respect to a single region of interest or each of a plurality of regions of interest. Specifically, information in which the time interval is associated with the hue is stored in the data storage unit 335, and the generating unit 334c changes the hue with reference to the information. Thus, the operator, the doctor, or the like can more clearly recognize, for example, a disease whose feature is in the interval of the reaching time.

The X-ray CT apparatus 30 according to the fourth embodiment may change the hue after generating the hue conversion image and the hue conversion table. In this case, when the hue of the hue conversion table is changed, the generating unit 334c changes the hue of the generated hue conversion image based on the changed hue conversion table. Thus, the operator, the doctor, or the like can clearly recognize a disease or the like since the regions difficult to discriminate can be made clear.

The X-ray CT apparatus 30 according to the fourth embodiment may use a two-dimensional or three-dimensional X-ray CT image. In this case, the hue conversion image may be used, for example, as a rendering image from a certain designation direction or displayed by a Multi Planar Reformation (MPR) image cut by a predetermined cross section.

According to the fourth embodiment, the image processing unit 334 generates the X-ray CT image. Then, the deciding unit 334b detects the reaching time at which the contrast agent has reached the predetermined region of the X-ray CT image. Further, the deciding unit 334b sets the color map in which the reaching time is associated with the hue based on the first inflow time corresponding to the first designation region set to the X-ray CT image and the second inflow time corresponding to the second designation region. Then, the generating unit 334c generates the hue conversion image in which the hue is allocated to each region of the X-ray CT image based on the color map and the reaching time in each region of the X-ray CT image. Then, the system control unit 333 displays the hue conversion image on the display unit 332. Thus, the X-ray CT apparatus 30 according to the fourth embodiment can image the dominant regions of different vascular channels with different hues, so that the dominant regions of different vascular channels can be easily discriminated.

Further, according to the fourth embodiment, the generating unit 334c generates the hue conversion table in which hues allocated in the hue conversion image are represented along a time axis. The system control unit 333 further displays the hue conversion table on the display unit 332. Thus, the X-ray CT apparatus 30 according to the fourth embodiment can make a relation between an inflow time of the contrast agent and the hue clear.

Further, according to the fourth embodiment, the detecting unit 334a detects the reaching time using the CT values of pixels included in the region of interest. Thus, the X-ray CT apparatus 30 according to the fourth embodiment can decide the reaching time of the contrast agent by a simple method without using raw data.

Further, according to the fourth embodiment, the deciding unit 334b determines the time at which a ratio of the number of pixels configuring the region of interest and having a CT value having reached the predetermined CT value has exceeded the predetermined threshold value as the reaching time. Alternatively, the deciding unit 334b determines the time at which the average CT value that is an average of CT values of pixels configuring the region of interest has exceeded the predetermined threshold as the reaching time. Thus, the X-ray CT apparatus 30 according to the fourth embodiment can variously set the reaching time of the contrast agent and flexibly execute an examination.

Further, according to the fourth embodiment, the generating unit 334c generates the frequency distribution in which the reaching time or the hue on the hue conversion image in pixels included in the X-ray CT image or the region of interest is associated with the number of pixels. The system control unit 333 displays the frequency distribution generated by the generating unit 334c on the display unit 332. Thus, the X-ray CT apparatus 30 according to the fourth embodiment can help the doctor make a more accurate determination on the CT examination using the contrast agent.

Further, according to the fourth embodiment, the generating unit 334c generates the hue conversion image after correcting the deviations between the X-ray CT images used for generating the hue conversion image. Thus, the X-ray CT apparatus 30 according to the fourth embodiment can generate the hue conversion image that is not influenced by the shaking of a moving body or the like and that is accurately consistent with the examination target portion.

Further, according to the fourth embodiment, the deciding unit 334b decides each of the reaching times at which the CT value detected by the detecting unit 334a has reached a plurality of different threshold values. By changing the hue at the new reaching time decided by the deciding unit 334b, the generating unit 334c generates the hue conversion image in which regions having reached a predetermined threshold at different reaching times are represented by different hues. Thus, the X-ray CT apparatus 30 according to the fourth embodiment can image dominant regions of different vascular channels with different hues even when it is difficult to designate two regions of interest in a region in which the vascular regions are concentrated or the like, so that the dominant regions of different vascular channels can be easily discriminated.

The example of using the X-ray CT apparatus as the medical image diagnosis apparatus has been described above. The contents of the description in the third embodiment can be appropriately applied to the X-ray CT apparatus 30 according to the fourth embodiment.

As described above, according to the first to fourth embodiment, a medical image diagnosis apparatus according to the present embodiment can image dominant regions of different vascular channels by a simple operation and easily discriminate dominant regions of different vascular channels.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnosis apparatus, comprising:
   an image processing unit configured to generate a medical image;
   a time detecting unit configured to detect a reaching time at which a contrast agent has reached a predetermined region of the medical image;
   a color map setting unit configured to set a color map in which the reaching time is associated with a hue based on a first inflow time corresponding to a first designation region set to the medical image and a second inflow time corresponding to a second designation region;
   a generating unit configured to generate a hue conversion image in which a hue is allocated to each region of the medical image based on the color map and the reaching time in each region of the medical image; and
   a display control unit configured to display the hue conversion image through a predetermined display unit.

2. The medical image diagnosis apparatus according to claim 1,
   wherein the color map setting unit sets a color map in which a reaching time between the first inflow time and the second inflow time is associated with a first hue, and a reaching time after the second inflow time is associated with a second hue.

3. The medical image diagnosis apparatus according to claim 1,
   wherein the generating unit further generates hue conversion information in which hues allocated in the hue conversion image are represented along a time axis, and
   the display control unit further displays the hue conversion information on the predetermined display unit.

4. The medical image diagnosis apparatus according to claim 1,
   wherein the time detecting unit detects the reaching time using brightness of a pixel included in the designation region.

5. The medical image diagnosis apparatus according to claim 4,
   wherein the time detecting unit determines a time at which a ratio of the number of pixels whose brightness has reached a predetermined brightness among pixels configuring the designation region has exceeded a predetermined threshold value as the reaching time or determines a time at which average brightness that is an average of brightness of the pixels configuring the designation region has exceeded a predetermined threshold value as the reaching time.

6. The medical image diagnosis apparatus according to claim 1,
   wherein the time detecting unit detects the reaching time in a moved designation region again when the position of the designation region on the medical image has moved, and
   the generating unit converts the hue conversion image into an image in which a hue is changed based on the reaching time detected again by the time detecting unit.

7. The medical image diagnosis apparatus according to claim 1,
   wherein the generating unit changes a hue to use according to an interval of the time detected by the time detecting unit on each of the first and second designation regions.

8. The medical image diagnosis apparatus according to claim 1,
   wherein even when a single designation region including the first and second designation regions is set,
   the time detecting unit detects each of reaching times at which brightness of the pixel has reached a plurality of different threshold values, and
   the generating unit changes a hue at a new reaching time detected by the time detecting unit and generates a hue conversion image in which regions having reached a predetermined threshold value at different reaching times are represented by different hues.

9. The medical image diagnosis apparatus according to claim 4,
   wherein the generating unit generates a frequency distribution in which the reaching time in a pixel configuring the medical image or the designation region or a hue on the hue conversion image is associated with the number of pixels, and
   the display control unit displays the frequency distribution generated by the generating unit through the predetermined display unit.

10. The medical image diagnosis apparatus according to claim 1,
    wherein the generating unit generate the hue conversion image after deviation between medical images used for generating the hue conversion image is corrected.

11. The medical image diagnosis apparatus according to claim 3,
    wherein the generating unit updates the hue conversion image based on changed hue conversion information when the hue conversion information is changed.

12. The medical image diagnosis apparatus according to claim 1,
    wherein the medical image is a two-dimensional or three-dimensional medical image.

13. A image processing apparatus, comprising:
    an image processing unit configured to generate a medical image;
    a time detecting unit configured to detect a reaching time at which a contrast agent has reached a predetermined region of the medical image;
    a color map setting unit configured to set a color map in which the reaching time is associated with a hue based on a first inflow time corresponding to a first designation region set to the medical image and a second inflow time corresponding to a second designation region;
    a generating unit configured to generate a hue conversion image in which a hue is allocated to each region of the medical image based on the color map and the reaching time in each region of the medical image; and
    a display control unit configured to display the hue conversion image through a predetermined display unit.

14. An image processing method, comprising:
    generating a medical image;
    detecting a reaching time at which a contrast agent has reached a predetermined region of the medical image;
    setting a color map in which the reaching time is associated with a hue based on a first inflow time corresponding to a first designation region set to the medical image and a second inflow time corresponding to a second designation region;

generating a hue conversion image in which a hue is allocated to each region of the medical image based on the color map and the reaching time in each region of the medical image; and displaying the hue conversion image through a predetermined display unit.

* * * * *